US010081783B2

(12) United States Patent
Lant et al.

(10) Patent No.: US 10,081,783 B2
(45) Date of Patent: Sep. 25, 2018

(54) CLEANING COMPOSITIONS HAVING AN ENZYME SYSTEM

(71) Applicant: The Procter & Gamble Company, Cincinnati, OH (US)

(72) Inventors: Neil Joseph Lant, Newcastle upon Tyne (GB); Montserrat Guadalupe Vasquez Valdivieso, Newcastle upon Tyne (GB)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 15/613,365

(22) Filed: Jun. 5, 2017

(65) Prior Publication Data

US 2017/0355931 A1 Dec. 14, 2017

Related U.S. Application Data

(60) Provisional application No. 62/347,666, filed on Jun. 9, 2016.

(51) Int. Cl.

| | |
|---|---|
| ***C12N 9/24*** | (2006.01) |
| ***C09K 8/70*** | (2006.01) |
| ***C11D 3/386*** | (2006.01) |
| ***C11D 3/20*** | (2006.01) |
| ***C11D 3/39*** | (2006.01) |
| *C11D 3/00* | (2006.01) |
| *C11D 9/00* | (2006.01) |

(52) U.S. Cl.

CPC ............ *C11D 3/386* (2013.01); *C11D 3/2079* (2013.01); *C11D 3/38636* (2013.01); *C11D 3/3932* (2013.01); *C11D 3/00* (2013.01); *C11D 9/00* (2013.01)

(58) Field of Classification Search

CPC ................................ C12N 9/2491; C09K 8/70

See application file for complete search history.

(56) References Cited

U.S. PATENT DOCUMENTS

| | | | |
|---|---|---|---|
| 5,395,541 | A | 3/1995 | Carpenter et al. |
| 8,617,542 | B2 | 12/2013 | Madhyastha et al. |
| 9,205,133 | B2 | 12/2015 | Dawson et al. |
| 9,675,736 | B2 | 6/2017 | Burgess et al. |
| 2009/0130082 | A1 | 5/2009 | Kaplan |
| 2014/0073547 | A1 | 3/2014 | Meek et al. |
| 2015/0299623 | A1 | 10/2015 | Gori et al. |
| 2016/0319224 | A1 | 11/2016 | Lant et al. |
| 2016/0319225 | A1 | 11/2016 | Lant et al. |
| 2016/0319226 | A1 | 11/2016 | Lant et al. |
| 2016/0319227 | A1 | 11/2016 | Lant et al. |
| 2016/0319228 | A1 | 11/2016 | Lant et al. |
| 2017/0107457 | A1 | 4/2017 | Gori et al. |
| 2017/0152462 | A1 | 6/2017 | Baltsen et al. |
| 2017/0183643 | A1 | 6/2017 | Krogh et al. |

FOREIGN PATENT DOCUMENTS

| | | |
|---|---|---|
| WO | WO 2001023534 | 4/2001 |
| WO | WO 2015185689 | 12/2015 |

OTHER PUBLICATIONS

Nijland et al., PLoS ONE 5:E15668-E15668, 2010.*

Database UniProtKB [Online] Jan. 9, 2013 (Jan. 9, 2013), "SubName: Full=Endo-beta-1,6-galactanase {ECO:0000313:EMBL:CCK29791. 1}; EC=3. 2 .1.164 {ECO:0000313: EMBL:CCK29791.1};", XP002774287, retrieved from Uniprot Database accession No. K4R0H9 the whole document.

PCT Search Report for application No. PCT/US2017/036301, dated Oct. 18, 2017, 17 pages.

* cited by examiner

*Primary Examiner* — Maryam Monshipouri

(74) *Attorney, Agent, or Firm* — Gregory S. Darley-Emerson

(57) ABSTRACT

Cleaning compositions having an enzyme system, where the enzyme system includes a nuclease enzyme, an extracellular-polymer-degrading enzyme, and a cleaning adjunct. Methods of making and using such cleaning compositions. Use of an extracellular-polymer-degrading enzyme.

20 Claims, No Drawings

Specification includes a Sequence Listing.

CLEANING COMPOSITIONS HAVING AN ENZYME SYSTEM

FIELD OF THE INVENTION

The present disclosure relates to cleaning compositions that have an enzyme system. The present disclosure also relates to methods of making and using such cleaning compositions. The present disclosure also relates to the use of an extracellular-polymer-degrading enzyme.

BACKGROUND OF THE INVENTION

The detergent formulator is constantly aiming to improve the performance of cleaning compositions. Enzymes such as proteases, amylases, and lipases are known to provide useful cleaning benefits. However, enzymes work only on particular substrates, and when access to those target substrates is blocked by other soil materials, the efficiency of the enzymes is reduced.

There is a need for improved cleaning compositions that contain enzymes.

SUMMARY OF THE INVENTION

The present disclosure relates to cleaning compositions that include an enzyme system. The enzyme system may include a nuclease enzyme, an extracellular-polymer-degrading enzyme, and a cleaning adjunct. The extracellular-polymer-degrading enzyme may include: (i) a microbial endo-beta-1,6-galactanase; (ii) a mannanase with greater than about 60% identity to SEQ. ID NO. 9 (*Ascobolus stictoideus*); (iii) a mannanase with greater than about 60% identity to SEQ. ID NO. 10 (*Chaetomium virescens*); (iv) a TY145 protease with greater than about 63% identity to SEQ. ID NO. 11; (v) a PcuAmyl α-amylase with greater than about 60% identity to SEQ. ID NO. 13; or (vi) combinations thereof. The enzyme system and/or cleaning adjunct may include a protease, an amylase, a lipase, or a combination thereof. The cleaning adjunct may include a surfactant system, among other things.

The present disclosure also relates to a method of cleaning a surface, preferably a textile, where the method includes mixing the cleaning composition according to the present disclosure with water to form an aqueous liquor and contacting a surface, preferably a textile, with the aqueous liquor in a laundering step.

The present disclosure also relates to the use of an extracellular-polymer-degrading enzyme in a cleaning composition to enhance the stain-removal and/or malodor-reducing benefits of a nuclease enzyme.

DETAILED DESCRIPTION OF THE INVENTION

The present disclosure relates to cleaning compositions that include an enzyme system, which includes a nuclease enzyme, an extracellular-polymer-degrading enzyme, and additional enzyme(s). Without wishing to be bound by theory, it is believed that the nuclease and the extracellular-polymer-degrading enzyme work synergistically to remove certain soil materials, thereby enabling better access of other cleaning adjuncts, including other enzymes, to their respective target soils, resulting in improved soil removal.

The components of the compositions and processes of the present disclosure are described in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used herein, the term "alkoxy" is intended to include C1-C8 alkoxy and C1-C8 alkoxy derivatives of polyols having repeating units such as butylene oxide, glycidol oxide, ethylene oxide or propylene oxide.

As used herein, unless otherwise specified, the terms "alkyl" and "alkyl capped" are intended to include C1-C18 alkyl groups, or even C1-C6 alkyl groups.

As used herein, unless otherwise specified, the term "aryl" is intended to include C3-12 aryl groups.

As used herein, unless otherwise specified, the term "arylalkyl" and "alkaryl" are equivalent and are each intended to include groups comprising an alkyl moiety bound to an aromatic moiety, typically having C1-C18 alkyl groups and, in one aspect, C1-C6 alkyl groups.

The terms "ethylene oxide," "propylene oxide" and "butylene oxide" may be shown herein by their typical designation of "EO," "PO" and "BO," respectively.

As used herein, the term "cleaning and/or treatment composition" includes, unless otherwise indicated, granular, powder, liquid, gel, paste, unit dose, bar form and/or flake type washing agents and/or fabric treatment compositions, including but not limited to products for laundering fabrics, fabric softening compositions, fabric enhancing compositions, fabric freshening compositions, and other products for the care and maintenance of fabrics, and combinations thereof. Such compositions may be pre-treatment compositions for use prior to a washing step or may be rinse added compositions, as well as cleaning auxiliaries, such as bleach additives and/or "stain-stick" or pre-treat compositions or substrate-laden products such as dryer added sheets.

As used herein, "cellulosic substrates" are intended to include any substrate which comprises cellulose, either 100% by weight cellulose or at least 20% by weight, or at least 30% by weight or at least 40 or at least 50% by weight or even at least 60% by weight cellulose. Cellulose may be found in wood, cotton, linen, jute, and hemp. Cellulosic substrates may be in the form of powders, fibers, pulp and articles formed from powders, fibers and pulp. Cellulosic fibers, include, without limitation, cotton, rayon (regenerated cellulose), acetate (cellulose acetate), triacetate (cellulose triacetate), and mixtures thereof. Typically cellulosic substrates comprise cotton. Articles formed from cellulosic fibers include textile articles such as fabrics. Articles formed from pulp include paper.

As used herein, the term "maximum extinction coefficient" is intended to describe the molar extinction coefficient at the wavelength of maximum absorption (also referred to herein as the maximum wavelength), in the range of 400 nanometers to 750 nanometers.

As used herein "average molecular weight" is reported as a weight average molecular weight, as determined by its molecular weight distribution; as a consequence of their manufacturing process, polymers disclosed herein may contain a distribution of repeating units in their polymeric moiety.

As used herein the term "variant" refers to a polypeptide that contains an amino acid sequence that differs from a wild type or reference sequence. A variant polypeptide can differ from the wild type or reference sequence due to a deletion, insertion, or substitution of a nucleotide(s) relative to said reference or wild type nucleotide sequence. The reference or wild type sequence can be a full-length native polypeptide sequence or any other fragment of a full-length polypeptide sequence. A polypeptide variant generally has at least about 70% amino acid sequence identity with the reference sequence, but may include 75% amino acid sequence identity within the reference sequence, 80% amino acid sequence identity within the reference sequence, 85% amino acid sequence identity with the reference sequence, 86% amino acid sequence identity with the reference sequence, 87% amino acid sequence identity with the reference sequence, 88% amino acid sequence identity with the reference sequence, 89% amino acid sequence identity with the reference sequence, 90% amino acid sequence identity with the reference sequence, 91% amino acid sequence identity with the reference sequence, 92% amino acid sequence identity with the reference sequence, 93% amino acid sequence identity with the reference sequence, 94% amino acid sequence identity with the reference sequence, 95% amino acid sequence identity with the reference sequence, 96% amino acid sequence identity with the reference sequence, 97% amino acid sequence identity with the reference sequence, 98% amino acid sequence identity with the reference sequence, 98.5% amino acid sequence identity with the reference sequence or 99% amino acid sequence identity with the reference sequence.

As used herein, the term "solid" includes granular, powder, bar and tablet product forms.

As used herein, the term "fluid" includes liquid, gel, paste, and gas product forms.

Cleaning Composition

The present disclosure relates to cleaning compositions. The cleaning composition may be selected from the group of light duty liquid detergents compositions, heavy duty liquid detergent compositions, hard surface cleaning compositions, detergent gels commonly used for laundry, bleaching compositions, laundry additives, fabric enhancer compositions, shampoos, body washes, other personal care compositions, and mixtures thereof. The cleaning composition may be a hard surface cleaning composition (such as a dishwashing composition) or a laundry composition (such as a heavy duty liquid detergent composition).

The cleaning compositions may be in any suitable form. The composition can be selected from a liquid, solid, or combination thereof. As used herein, "liquid" includes free-flowing liquids, as well as pastes, gels, foams and mousses. Non-limiting examples of liquids include light duty and heavy duty liquid detergent compositions, fabric enhancers, detergent gels commonly used for laundry, bleach and laundry additives. Gases, e.g., suspended bubbles, or solids, e.g. particles, may be included within the liquids. A "solid" as used herein includes, but is not limited to, powders, agglomerates, and mixtures thereof. Non-limiting examples of solids include: granules, micro-capsules, beads, noodles, and pearlised balls. Solid compositions may provide a technical benefit including, but not limited to, through-the-wash benefits, pre-treatment benefits, and/or aesthetic effects.

The cleaning composition may be in the form of a unitized dose article, such as a tablet or in the form of a pouch. Such pouches typically include a water-soluble film, such as a polyvinyl alcohol water-soluble film, that at least partially encapsulates a composition. Suitable films are available from MonoSol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch may be liquid, solid (such as powders), or combinations thereof.

Enzyme System

The cleaning compositions of the present disclosure comprise an enzyme system. The enzyme system may be present in the cleaning composition at a level of from about 0.0001% to about 5%, or from about 0.001% to about 2%, by weight of the cleaning composition.

The enzyme system comprises a plurality of enzymes. The enzymes may be provided individually, or they may be provided as a combination, such as in a premix that contains a plurality of enzymes.

The enzyme system may comprise a nuclease enzyme and an extracellular-polymer-degrading enzyme. The system may further comprise an additional enzyme. The extracellular-polymer-degrading enzyme may be selected from the group consisting of: (i) a microbial endo-beta-1,6-galactanase; (ii) a mannanase with greater than about 60% identity to SEQ. ID NO. 9 (*Ascobolus stictoideus*); (iii) a mannanase with greater than about 60% identity to SEQ. ID NO. 10 (*Chaetomium virescens*); (iv) a TY145 protease with greater than 63% identity to SEQ. ID NO. 11; (v) a PcuAmyl α-amylase with greater than 60% identity to SEQ. ID NO. 13; and (vi) combinations thereof. The enzyme system may comprise an additional enzyme. The additional enzyme may include a protease, an amylase, a lipase, or a combination thereof. These enzymes are discussed in more detail below.

Nuclease Enzyme

The enzyme system may comprise a nuclease enzyme. The nuclease enzyme is an enzyme capable of cleaving the phosphodiester bonds between the nucleotide sub-units of nucleic acids. The nuclease enzyme herein is preferably a deoxyribonuclease or ribonuclease enzyme or a functional fragment thereof. By functional fragment or part is meant the portion of the nuclease enzyme that catalyzes the cleavage of phosphodiester linkages in the DNA backbone and so is a region of said nuclease protein that retains catalytic activity. Thus it includes truncated, but functional versions, of the enzyme and/or variants and/or derivatives and/or homologues whose functionality is maintained.

Preferably the nuclease enzyme is a deoxyribonuclease, preferably selected from any of the classes E.C. 3.1.21.x, where x=1, 2, 3, 4, 5, 6, 7, 8 or 9, E.C. 3.1.22.y where y=1, 2, 4 or 5, E.C. 3.1.30.z where z=1 or 2, E.C. 3.1.31.1 and mixtures thereof.

Nucleases in class E.C. 3.1.21.x cleave at the 3' hydroxyl to liberate 5' phosphomonoesters as follows:

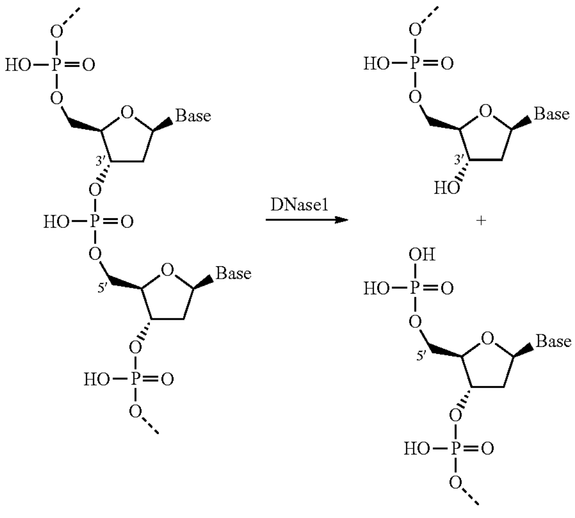

Nuclease enzymes from class E.C. 3.1.21.x and especially where x=1 are particularly preferred.

Nucleases in class E.C. 3.1.22.y cleave at the 5' hydroxyl to liberate 3' phosphomonoesters. Enzymes in class E.C. 3.1.30.z may be preferred as they act on both DNA and RNA and liberate 5'-phosphomonoesters. Suitable examples from class E.C. 3.1.31.2 are described in US2012/0135498A, such as SEQ ID NO:3 therein. Such enzymes are commercially available as DENARASE® enzyme from c-LECTA.

Nuclease enzymes from class E.C. 3.1.31.1 produce 3'phosphomonoesters.

Preferably, the nuclease enzyme comprises a microbial enzyme. The nuclease enzyme may be fungal or bacterial in origin. Bacterial nucleases may be most preferred. Fungal nucleases may be most preferred.

The microbial nuclease may be obtainable from *Bacillus*, such as a *Bacillus licheniformis* or *Bacillus subtilis* bacterial nucleases. A preferred nuclease is obtainable from *Bacillus licheniformis*, preferably from strain EI-34-6. A preferred deoxyribonuclease is a variant of *Bacillus licheniformis*, from strain EI-34-6 nucB deoxyribonuclease defined in SEQ ID NO:1 herein, or variant thereof, for example having at least 70% or 75% or 80% or 85% or 90% or 95%, 96%, 97%, 98%, 99% or 100% identical thereto.

Other suitable nucleases are defined in SEQ ID NO:2 herein, or variant thereof, for example having at least 70% or 75% or 80% or 85% or 90% or 95%, 96%, 97%, 98%, 99% or 100% identical thereto. Other suitable nucleases are defined in SEQ ID NO:3 herein, or variant thereof, for example having at least 70% or 75% or 80% or 85% or 90% or 95%, 96%, 97%, 98%, 99% or 100% identical thereto.

A fungal nuclease is obtainable from *Aspergillus*, for example *Aspergillus oryzae*. A preferred nuclease is obtainable from *Aspergillus oryzae* defined in SEQ ID NO: 5 herein, or variant thereof, for example having at least 60% or 70% or 75% or 80% or 85% or 90% or 95%, 96%, 97%, 98%, 99% or 100% identical thereto.

Another suitable fungal nuclease is obtainable from *Trichoderma*, for example *Trichoderma harzianum*. A preferred nuclease is obtainable from *Trichoderma harzianum* defined in SEQ ID NO: 6 herein, or variant thereof, for example having at least 60% or 70% or 75% or 80% or 85% or 90% or 95%, 96%, 97%, 98%, 99% or 100% identical thereto.

Other fungal nucleases include those encoded by the DNA sequences of *Aspergillus oryzae* RIB40, *Aspergillus oryzae* 3.042, *Aspergillus flavus* NRRL3357, *Aspergillus parasiticus* SU-1, *Aspergillus nomius* NRRL13137, *Trichoderma reesei* QM6a, *Trichoderma virens* Gv29-8, *Oidiodendron maius* Zn, *Metarhizium guizhouense* ARSEF 977, *Metarhizium majus* ARSEF 297, *Metarhizium robertsii* ARSEF 23, *Metarhizium acridum* CQMa 102, *Metarhizium brunneum* ARSEF 3297, *Metarhizium anisopliae*, *Colletotrichum fioriniae* PJ7, *Colletotrichum sublineola*, *Trichoderma atroviride* IMI 206040, *Tolypocladium ophioglossoides* CBS 100239, *Beauveria bassiana* ARSEF 2860, *Colletotrichum higginsianum*, *Hirsutella minnesotensis* 3608, *Scedosporium apiospermum*, *Phaeomoniella chlamydospora*, *Fusarium verticillioides* 7600, *Fusarium oxysporum* f. sp. *cubense* race 4, *Colletotrichum graminicola* M1.001, *Fusarium oxysporum* FOSC 3-a, *Fusarium avenaceum*, *Fusarium langsethiae*, *Grosmannia clavigera* kw1407, *Claviceps purpurea* 20.1, *Verticillium longisporum*, *Fusarium oxysporum* f. sp. *cubense* race 1, *Magnaporthe oryzae* 70-15, *Beauveria bassiana* D1-5, *Fusarium pseudograminearum* CS3096, *Neonectria ditissima*, *Magnaporthiopsis poae* ATCC 64411, *Cordyceps militaris* CM01, *Marssonina brunnea* f. sp. 'multigermtubi' MB_ml, *Diaporthe ampelina*, *Metarhizium album* ARSEF 1941, *Colletotrichum gloeosporioides* Nara gc5, *Madurella mycetomatis*, *Metarhizium brunneum* ARSEF 3297, *Verticillium alfalfae* VaMs.102, *Gaeumannomyces graminis* var. *tritici* R3-111a-1, *Nectria haematococca* mpVI 77-13-4, *Verticillium longisporum*, *Verticillium dahliae* VdLs.17, *Torrubiella hemipterigena*, *Verticillium longisporum*, *Verticillium dahliae* VdLs.17, *Botrytis cinerea* B05.10, *Chaetomium globosum* CBS 148.51, *Metarhizium anisopliae*, *Stemphylium lycopersici*, *Sclerotinia borealis* F-4157, *Metarhizium robertsii* ARSEF 23, *Myceliophthora thermophila* ATCC 42464, *Phaeosphaeria nodorum* SN15, *Phialophora attae*, *Ustilaginoidea virens*, *Diplodia seriata*, *Ophiostoma piceae* UAMH 11346, *Pseudogymnoascus pannorum* VKM F-4515 (FW-2607), *Bipolaris oryzae* ATCC 44560, *Metarhizium guizhouense* ARSEF 977, *Chaetomium thermophilum* var. *thermophilum* DSM 1495, *Pestalotiopsis fici* W106-1, *Bipolaris zeicola* 26-R-13, *Setosphaeria turcica* Et28A, *Arthroderma otae* CBS 113480 and *Pyrenophora tritici-repentis* Pt-1C-BFP.

Preferably the nuclease is an isolated nuclease.

Preferably the nuclease enzyme is present in a the laundering aqueous solution in an amount of from 0.01 ppm to 1000 ppm of the nuclease enzyme, or from 0.05 or from 0.1 ppm to 750 or 500 ppm.

The nucleases may also give rise to biofilm-disrupting effects.

In a preferred composition, the composition additionally comprises a 13-N-acetylglucosaminidase enzyme from E.C. 3.2.1.52, preferably an enzyme having at least 70%, or at least 75% or at least 80% or at least 85% or at least 90% or at least 95% or at least 96% or at least 97% or at least 98% or at least 99% or at least or 100% identity to SEQ ID NO:4.

Endo-beta-1,6-galactanase

The enzyme system may comprise an extracellular polymer-degrading enzyme that includes an endo-beta-1,6-galactanase enzyme. The term "endo-beta-1,6-galactanase" or "a polypeptide having endo-beta-1,6-galactanase activity" means a endo-beta-1,6-galactanase activity (EC 3.2.1.164) that catalyzes the hydrolytic cleavage of 1,6-3-D-galactooligosaccharides with a degree of polymerization (DP) higher than 3, and their acidic derivatives with 4-O-methylglucosyluronate or glucosyluronate groups at the non-reducing terminals.

For purposes of the present disclosure, endo-beta-1,6-galactanase activity is determined according to the procedure described in WO 2015185689 in Assay I.

Suitable examples from class EC 3.2.1.164 are described in WO 2015185689, such as the mature polypeptide SEQ ID NO: 2.

Preferably, the endo-beta-1,6-galactanase comprises a microbial enzyme. The endo-beta-1,6-galactanase may be fungal or bacterial in origin. Bacterial endo-beta-1,6-galactanase may be most preferred. Fungal endo-beta-1,6-galactanase may be most preferred.

A bacterial endo-beta-1,6-galactanase is obtainable from *Streptomyces*, for example *Streptomyces davawensis*. A preferred endo-beta-1,6-galactanase is obtainable from *Streptomyces davawensis* JCM 4913 defined in SEQ ID NO 7 herein, or variant thereof, for example having at least 40 or 50% or 60% or 70% or 75% or 80% or 85% or 90% or 95%, 96%, 97%, 98%, 99% or 100% identical thereto.

Other bacterial endo-beta-1,6-galactanase include those encoded by the DNA sequences of *Streptomyces avermitilis* MA-4680.

A fungal endo-beta-1,6-galactanase is obtainable from *Trichoderma*, for example *Trichoderma harzianum*. A preferred endo-beta-1,6-galactanase is obtainable from *Trichoderma harzianum* defined in SEQ ID NO 8 herein, or variant thereof, for example having at least 40 or 50% or 60% or 70% or 75% or 80% or 85% or 90% or 95%, 96%, 97%, 98%, 99% or 100% identical thereto.

Other fungal endo-beta-1,6-galactanase include those encoded by the DNA sequences of *Ceratocystis fimbriate* f. sp. *Platani, Muscodor strobelii* WG-2009a, *Oculimacula yallundae, Trichoderma viride* GD36A, *Thermomyces stellatus, Myceliophthora thermophilia.*

Mannanase

The enzyme system may comprise an extracellular-polymer-degrading enzyme that includes a mannanase enzyme. The term "mannanase" means a polypeptide having mannan endo-1,4-beta-mannosidase activity (EC 3.2.1.78) that catalyzes the hydrolysis of 1,4-3-D-mannosidic linkages in mannans, galactomannans and glucomannans. Alternative names of mannan endo-1,4-beta-mannosidase are 1,4-3-D-mannan mannanohydrolase; endo-1,4-3-mannanase; endo-β-1,4-mannase; β-mannanase B; 3-1,4-mannan 4-mannanohydrolase; endo-3-mannanase; and β-D-mannanase.

For purposes of the present disclosure, mannanase activity may be determined using the Reducing End Assay as described in the experimental section of WO 2015040159.

Suitable examples from class EC 3.2.1.78 are described in WO 2015040159, such as the mature polypeptide SEQ ID NO:x1 described therein.

A polypeptide having at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO 9 from *Ascobolus stictoideus;*

A polypeptide having at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the mature polypeptide SEQ ID NO 10 from *Chaetomium virescens.*

Protease

The enzyme system may comprise a protease enzyme. The protease enzyme may comprise a subtilase enzyme.

The term "subtilases" refer to a sub-group of serine protease according to Siezen et al., Protein Engng. 4 (1991) 719-737 and Siezen et al. Protein Science 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. Subtilases are defined by homology analysis of more than 170 amino acid sequences of serine proteases previously referred to as subtilisin-like proteases. The subtilases may be divided into 6 sub-divisions, i.e. the Subtilisin family, the Thermitase family, the Proteinase K family, the Lantibiotic peptidase family, the Kexin family and the Pyrolysin family. The Subtilisin family (EC 3.4.21.62) may be further divided into 3 sub-groups, i.e. I-S1 ("true" subtilisins), I-S2 (highly alkaline proteases) and intracellular subtilisins.

A TY145 subtilase or TY145 type subtilase is in the context of the present disclosure to be understood as a subtilase which has at least 63% identity to SEQ ID NO 11. In particular said TY145 subtilase may have at least 65%, such as at least 70%, at least 74%, at least 80%, at least 83%, at least 90%, at least 91%, at least 92%, at least 93%, at least 94%, at least 95%, at least 96%, at least 97%, at least 98% or at least 99% identity to TY145, i.e. to SEQ ID NO 11.

Examples of subtilases of the TY145 type include the TY145 subtilase, the psychrophilic subtilisin protease S41 derived from the Antarctic *Bacillus* TA41, herein also called TA41 subtilase (Davail S et al., 1994, J. Biol. Chem., 269, 17448-17453), and the psychrophilic subtilisin protease S39 derived from the Antarctic *Bacillus* TA39, herein also called TA39 subtilase (Narinx E et al., 1997, Protein Engineering, 10 (11), 1271-1279).

Additionally, a protease variant comprising substitution at positions S3T, V4I, R99D/E, A188P and V199I, preferably S3T, V4I, R99E, A188P and V199I, of SEQ ID NO 12, wherein the variant has at least 70% and less than 100% sequence identity to SEQ ID NO 12.

Amylase

The enzyme system may comprise an amylase enzyme. The terms "amylase" or "amylolytic enzyme" refer to an enzyme that is, among other things, capable of catalyzing the degradation of starch. α-amylases are hydrolases that cleave the a-D-(1→4) β-glycosidic linkages in starch. Generally, α-amylases (EC 3.2.1.1; a-D-(1→4)-glucan glucanohydrolase) are defined as endo-acting enzymes cleaving a-D-(1→4) β-glycosidic linkages within the starch molecule in a random fashion yielding polysaccharides containing three or more (1-4)-a-linked D-glucose units. In contrast, the exo-acting amylolytic enzymes, such as β-amylases (EC 3.2.1.2; a-D-(1→4)-glucan maltohydrolase) and some product-specific amylases like maltogenic α-amylase (EC 3.2.1.133) cleave the polysaccharide/starch molecule from the non-reducing end of the substrate, β-amylases, a-glucosidases (EC 3.2.1.20; a-D-glucoside glucohydrolase), glucoamylase (EC 3.2.1.3; a-D-(1→4)-glucan glucohydrolase), and product-specific amylases like the maltotetraosidases (EC 3.2.1.60) and the maltohexaosidases (EC 3.2.1.98) can produce malto-oligosaccharides of a specific length or enriched syrups of specific maltooligosaccharides.

A "PcuAmyl α-amylase" is an amylase predicted from from *Paenibacillus curdlanolyticus* YK9 having at least 60% amino acid sequence identity to SEQ ID NO 13 and having amylase activity (as described above). For example, a PcuAmyl α-amylase having amylase activity can have at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence identity to SEQ ID NO 13.

Lipase

The enzyme system may comprise a lipase enzyme. The terms "lipase", "lipase enzyme", "lipolytic enzyme", "lipid esterase", "lipolytic polypeptide", and "lipolytic protein" refers to an enzyme in class EC3.1.1 as defined by Enzyme Nomenclature. It may have lipase activity (triacylglycerol lipase, EC3.1.1.3), cutinase activity (EC3.1.1.74), sterol esterase activity (EC3.1.1.13) and/or wax-ester hydrolase activity (EC3.1.1.50).

For purposes of the present disclosure, lipase activity is determined according to the procedure described in WO2014184164 in Examples.

The lipase variants of the present disclosure have higher than 95% sequence identity to the wild type SEQ ID NO 14 and comprise substitutions at positions corresponding to T231R+N233R and at least two or more of the following substitutions Q4V, D27R, N33Q, N33K, G38A, F51V, S54T, E56K, S58N, V605, L69R, G91Q, D96E, K98E, D111A, T143A, A150G, G163K, E210Q, E210K, Y220F, D2545, I255A, I255G, I255F, P256T of the polypeptide of SEQ ID NO 14, wherein the variant has lipase activity.

Cleaning Adjuncts

The cleaning compositions described herein may further include one or more cleaning adjuncts. Without wishing to be bound by theory, it is believed that the enzyme systems described herein promote the efficacy of the cleaning adjuncts by degrading certain polymeric soils, which in turn enables the cleaning adjuncts to access and remove more target soils and/or reaction products of the enzymatic reactions.

The cleaning adjunct may comprise a surfactant system as described below. Other suitable cleaning adjuncts include one or more components selected from the following non-limiting list of ingredients: fabric care benefit agent; detersive enzyme; deposition aid; rheology modifier; builder; chelant; bleach; bleaching agent; bleach precursor; bleach booster; bleach catalyst; perfume and/or perfume microcapsules; perfume loaded zeolite; starch encapsulated accord; polyglycerol esters; whitening agent; pearlescent agent; enzyme stabilizing systems; scavenging agents including fixing agents for anionic dyes, complexing agents for anionic surfactants, and mixtures thereof; optical brighteners or fluorescers; polymer including but not limited to soil release polymer and/or soil suspension polymer; dispersants; antifoam agents; non-aqueous solvent; fatty acid; suds suppressors, e.g., silicone suds suppressors; cationic starches; scum dispersants; substantive dyes; colorants; opacifier; antioxidant; hydrotropes such as toluenesulfonates, cumenesulfonates and naphthalenesulfonates; color speckles; colored beads, spheres or extrudates; clay softening agents; anti-bacterial agents. Additionally or alternatively, the compositions may comprise quaternary ammonium compounds, and/or solvent systems. Quaternary ammonium compounds may be present in fabric enhancer compositions, such as fabric softeners, and comprise quaternary ammonium cations that are positively charged polyatomic ions of the structure $NR_4^+$, where R is an alkyl group or an aryl group.

Surfactant System

The cleaning composition may comprise a surfactant system. The cleaning composition may comprise from about 1% to about 80%, or from 1% to about 60%, preferably from about 5% to about 50% more preferably from about 8% to about 40%, by weight of the cleaning composition, of a surfactant system.

Surfactants of the present surfactant system may be derived from natural and/or renewable sources.

The surfactant system may comprise an anionic surfactant, more preferably an anionic surfactant selected from the group consisting of alkyl sulfate, alkyl alkoxy sulfate, especially alkyl ethoxy sulfate, alkyl benzene sulfonate, paraffin sulfonate and mixtures thereof. The surfactant system may further comprise a surfactant selected from the group consisting of nonionic surfactant, cationic surfactant, amphoteric surfactant, zwitterionic surfactant, and mixtures thereof. The surfactant system may comprise an amphoteric surfactant; the amphoteric surfactant may comprise an amine oxide surfactant. The surfactant system may comprise a nonionic surfactant; the nonionic surfactant may comprise an ethoxylated nonionic surfactant.

Alkyl sulfates are preferred for use herein and also alkyl ethoxy sulfates; more preferably a combination of alkyl sulfates and alkyl ethoxy sulfates with a combined average ethoxylation degree of less than 5, preferably less than 3, more preferably less than 2 and more than 0.5 and an average level of branching of from about 5% to about 40%.

The composition of the invention comprises amphoteric and/or zwitterionic surfactant, preferably the amphoteric surfactant comprises an amine oxide, preferably an alkyl dimethyl amine oxide, and the zwitteronic surfactant comprises a betaine surfactant.

The most preferred surfactant system for the detergent composition of the present invention comprise from 1% to 40%, preferably 6% to 35%, more preferably 8% to 30% weight of the total composition of an anionic surfactant, preferably an alkyl alkoxy sulfate surfactant, more preferably an alkyl ethoxy sulfate, combined with 0.5% to 15%, preferably from 1% to 12%, more preferably from 2% to 10% by weight of the composition of amphoteric and/or zwitterionic surfactant, more preferably an amphoteric and even more preferably an amine oxide surfactant, especially and alkyl dimethyl amine oxide. Preferably the composition further comprises a nonionic surfactant, especially an alcohol alkoxylate in particular and alcohol ethoxylate nonionic surfactant.

Anionic Surfactant

Anionic surfactants include, but are not limited to, those surface-active compounds that contain an organic hydrophobic group containing generally 8 to 22 carbon atoms or generally 8 to 18 carbon atoms in their molecular structure and at least one water-solubilizing group preferably selected from sulfonate, sulfate, and carboxylate so as to form a water-soluble compound. Usually, the hydrophobic group will comprise a C8-C 22 alkyl, or acyl group. Such surfactants are employed in the form of water-soluble salts and the salt-forming cation usually is selected from sodium, potassium, ammonium, magnesium and mono-, di- or tri-C2-C3 alkanolammonium, with the sodium cation being the usual one chosen.

The anionic surfactant can be a single surfactant but usually it is a mixture of anionic surfactants. Preferably the anionic surfactant comprises a sulfate surfactant, more preferably a sulfate surfactant selected from the group consisting of alkyl sulfate, alkyl alkoxy sulfate and mixtures thereof. Preferred alkyl alkoxy sulfates for use herein are alkyl ethoxy sulfates.

Sulfated Anionic Surfactant

Preferably the sulfated anionic surfactant is alkoxylated, more preferably, an alkoxylated branched sulfated anionic surfactant having an alkoxylation degree of from about 0.2 to about 4, even more preferably from about 0.3 to about 3, even more preferably from about 0.4 to about 1.5 and especially from about 0.4 to about 1. Preferably, the alkoxy group is ethoxy. When the sulfated anionic surfactant is a mixture of sulfated anionic surfactants, the alkoxylation degree is the weight average alkoxylation degree of all the components of the mixture (weight average alkoxylation degree). In the weight average alkoxylation degree calculation the weight of sulfated anionic surfactant components not having alkoxylated groups should also be included.

Weight average alkoxylation degree=($x1$*alkoxylation degree of surfactant 1+$x2$*alkoxylation degree of surfactant 2+ . . . )/($x1$+$x2$+ . . . )

wherein x1, x2, . . . are the weights in grams of each sulfated anionic surfactant of the mixture and alkoxylation degree is the number of alkoxy groups in each sulfated anionic surfactant.

Preferably, the branching group is an alkyl. Typically, the alkyl is selected from methyl, ethyl, propyl, butyl, pentyl, cyclic alkyl groups and mixtures thereof. Single or multiple alkyl branches could be present on the main hydrocarbyl chain of the starting alcohol(s) used to produce the sulfated anionic surfactant used in the detergent of the invention. Most preferably the branched sulfated anionic surfactant is selected from alkyl sulfates, alkyl ethoxy sulfates, and mixtures thereof.

The branched sulfated anionic surfactant can be a single anionic surfactant or a mixture of anionic surfactants. In the case of a single surfactant the percentage of branching refers to the weight percentage of the hydrocarbyl chains that are branched in the original alcohol from which the surfactant is derived.

In the case of a surfactant mixture the percentage of branching is the weight average and it is defined according to the following formula:

Weight average of branching (%)=[($x1$*wt % branched alcohol 1 in alcohol 1+$x2$*wt % branched alcohol 2 in alcohol 2+ . . . )/($x1$+$x2$+ . . . )]*100 wherein x1, x2, . . . are the weight in grams of each alcohol in the total alcohol mixture of the alcohols which were used as starting material for the anionic surfactant for the detergent of the invention. In the weight average branching degree calculation the weight of anionic surfactant components not having branched groups should also be included.

Suitable sulfate surfactants for use herein include water-soluble salts of C8-C18 alkyl or hydroxyalkyl, sulfate and/or ether sulfate. Suitable counterions include alkali metal cation or ammonium or substituted ammonium, but preferably sodium.

The sulfate surfactants may be selected from C8-C18 primary, branched chain and random alkyl sulfates (AS); C8-C18 secondary (2,3) alkyl sulfates; C8-C18 alkyl alkoxy sulfates (AExS) wherein preferably x is from 1-30 in which the alkoxy group could be selected from ethoxy, propoxy, butoxy or even higher alkoxy groups and mixtures thereof.

Alkyl sulfates and alkyl alkoxy sulfates are commercially available with a variety of chain lengths, ethoxylation and branching degrees. Commercially available sulfates include, those based on Neodol alcohols ex the Shell company, Lial—Isalchem and Safol ex the Sasol company, natural alcohols ex The Procter & Gamble Chemicals company.

Preferably, the anionic surfactant comprises at least 50%, more preferably at least 60% and especially at least 70% of a sulfate surfactant by weight of the anionic surfactant. Especially preferred detergents from a cleaning view point are those in which the anionic surfactant comprises more than 50%, more preferably at least 60% and especially at least 70% by weight thereof of sulfate surfactant and the sulfate surfactant is selected from the group consisting of alkyl sulfates, alkyl ethoxy sulfates and mixtures thereof. Even more preferred are those in which the anionic surfactant is an alkyl ethoxy sulfate with a degree of ethoxylation of from about 0.2 to about 3, more preferably from about 0.3 to about 2, even more preferably from about 0.4 to about 1.5, and especially from about 0.4 to about 1. They are also preferred anionic surfactant having a level of branching of from about 5% to about 40%, even more preferably from about 10% to 35% and especially from about 20% to 30%.

Sulfonate Surfactant

Suitable anionic sulfonate surfactants for use herein include water-soluble salts of C8-C18 alkyl or hydroxyalkyl sulfonates; C11-C18 alkyl benzene sulfonates (LAS), modified alkylbenzene sulfonate (MLAS) as discussed in WO 99/05243, WO 99/05242, WO 99/05244, WO 99/05082, WO 99/05084, WO 99/05241, WO 99/07656, WO 00/23549, and WO 00/23548; methyl ester sulfonate (MES); and alpha-olefin sulfonate (AOS). Those also include the paraffin sulfonates may be monosulfonates and/or disulfonates, obtained by sulfonating paraffins of 10 to 20 carbon atoms. The sulfonate surfactant also include the alkyl glyceryl sulfonate surfactants.

Nonionic Surfactant

Nonionic surfactant, when present, is comprised in a typical amount of from 0.1% to 40%, preferably 0.2% to 20%, most preferably 0.5% to 10% by weight of the composition. Suitable nonionic surfactants include the condensation products of aliphatic alcohols with from 1 to 25 moles of ethylene oxide. The alkyl chain of the aliphatic alcohol can either be straight or branched, primary or secondary, and generally contains from 8 to 22 carbon atoms. Particularly preferred are the condensation products of alcohols having an alkyl group containing from 10 to 18 carbon atoms, preferably from 10 to 15 carbon atoms with from 2 to 18 moles, preferably 2 to 15, more preferably 5-12 of ethylene oxide per mole of alcohol. Highly preferred nonionic surfactants are the condensation products of guerbet alcohols with from 2 to 18 moles, preferably 2 to 15, more preferably 5-12 of ethylene oxide per mole of alcohol.

Other suitable non-ionic surfactants for use herein include fatty alcohol polyglycol ethers, alkylpolyglucosides and fatty acid glucamides.

Amphoteric Surfactant

The surfactant system may include amphoteric surfactant, such as amine oxide. Preferred amine oxides are alkyl dimethyl amine oxide or alkyl amido propyl dimethyl amine oxide, more preferably alkyl dimethyl amine oxide and especially coco dimethyl amino oxide. Amine oxide may have a linear or mid-branched alkyl moiety. Typical linear amine oxides include water-soluble amine oxides containing one R1 C8-18 alkyl moiety and 2 R2 and R3 moieties selected from the group consisting of C1-3 alkyl groups and C1-3 hydroxyalkyl groups. Preferably amine oxide is characterized by the formula R1-N(R2)(R3)O wherein R1 is a C8-18 alkyl and R2 and R3 are selected from the group consisting of methyl, ethyl, propyl, isopropyl, 2-hydroxethyl, 2-hydroxypropyl and 3-hydroxypropyl. The linear amine oxide surfactants in particular may include linear C10-C18 alkyl dimethyl amine oxides and linear C8-C12 alkoxy ethyl dihydroxy ethyl amine oxides. Preferred amine oxides include linear C10, linear C10-C12, and linear C12-C14 alkyl dimethyl amine oxides. As used herein "mid-branched" means that the amine oxide has one alkyl moiety having n1 carbon atoms with one alkyl branch on the alkyl moiety having n2 carbon atoms. The alkyl branch is located on the a carbon from the nitrogen on the alkyl moiety. This type of branching for the amine oxide is also known in the art as an internal amine oxide. The total sum of n1 and n2 is from 10 to 24 carbon atoms, preferably from 12 to 20, and more preferably from 10 to 16. The number of carbon atoms for the one alkyl moiety (n1) should be approximately the same number of carbon atoms as the one alkyl branch (n2) such that the one alkyl moiety and the one alkyl branch are symmetric. As used herein "symmetric" means that $|n1-n2|$ is less than or equal to 5, preferably 4, most preferably from 0 to 4 carbon atoms in at least 50 wt %, more preferably at least 75 wt % to 100 wt % of the mid-branched amine oxides for use herein.

The amine oxide further comprises two moieties, independently selected from a C1-3 alkyl, a C1-3 hydroxyalkyl group, or a polyethylene oxide group containing an average of from about 1 to about 3 ethylene oxide groups. Preferably the two moieties are selected from a C1-3 alkyl, more preferably both are selected as a C1 alkyl.

Zwitterionic Surfactant

Other suitable surfactants include betaines, such as alkyl betaines, alkylamidobetaine, amidazoliniumbetaine, sulfobetaine (INCI Sultaines) as well as the Phosphobetaine and preferably meets formula (I):

$$R^1—[CO—X(CH_2)_n]_x—N^+(R^2)(R_3)—(CH_2)_m—[CH(OH)—CH_2]_y—Y— \quad (I)$$

wherein $R^1$ is a saturated or unsaturated C6-22 alkyl residue, preferably C8-18 alkyl residue, in particular a saturated C10-16 alkyl residue, for example a saturated C12-14 alkyl residue;

X is NH, $NR^4$ with C1-4 Alkyl residue $R^4$, O or S, n a number from 1 to 10, preferably 2 to 5, in particular 3, x 0 or 1, preferably 1, $R^2$, $R^3$ are independently a C1-4 alkyl residue, potentially hydroxy substituted such as a hydroxyethyl, preferably a methyl.

m a number from 1 to 4, in particular 1, 2 or 3, y 0 or 1 and

Y is COO, SO3, $OPO(OR^5)O$ or $P(O)(OR^5)O$, whereby $R^5$ is a hydrogen atom H or a C1-4 alkyl residue.

Preferred betaines are the alkyl betaines of the formula (Ia), the alkyl amido propyl betaine of the formula (Ib), the Sulfo betaines of the formula (Ic) and the Amido sulfobetaine of the formula (Id);

$$R^1—N^+(CH_3)_2—CH_2COO^- \quad (Ia)$$

$$R^1—CO—NH(CH_2)_3—N^+(CH_3)_2—CH_2COO^- \quad (Ib)$$

$$R^1—N^+(CH_3)_2—CH_2CH(OH)CH_2SO_3— \quad (Ic)$$

$R^1—CO—NH—(CH_2)_3—N^+(CH_3)_2—CH_2CH(OH)CH_2SO_3—$ (Id) in which $R^1$1 as the same meaning as in formula I. Particularly preferred betaines are the Carbobetaine [wherein $Y^-$=$COO^-$], in particular the Carbobetaine of the formula (Ia) and (Ib), more preferred are the Alkylamidobetaine of the formula (Ib).

Examples of suitable betaines and sulfobetaine are the following [designated in accordance with INCI]: Almondamidopropyl of betaines, Apricotam idopropyl betaines, Avocadamidopropyl of betaines, Babassuamidopropyl of betaines, Behenam idopropyl betaines, Behenyl of betaines, betaines, Canolam idopropyl betaines, Capryl/Capram idopropyl betaines, Carnitine, Cetyl of betaines, Cocamidoethyl of betaines, Cocam idopropyl betaines, Cocam idopropyl Hydroxysultaine, Coco betaines, Coco Hydroxysultaine, Coco/Oleam idopropyl betaines, Coco Sultaine, Decyl of betaines, Dihydroxyethyl Oleyl Glycinate, Dihydroxyethyl Soy Glycinate, Dihydroxyethyl Stearyl Glycinate, Dihydroxyethyl Tallow Glycinate, Dimethicone Propyl of PG-betaines, Erucam idopropyl Hydroxysultaine, Hydrogenated Tallow of betaines, Isostearam idopropyl betaines, Lauram idopropyl betaines, Lauryl of betaines, Lauryl Hydroxysultaine, Lauryl Sultaine, Milkam idopropyl betaines, Minkamidopropyl of betaines, Myristam idopropyl betaines, Myristyl of betaines, Oleam idopropyl betaines, Oleam idopropyl Hydroxysultaine, Oleyl of betaines, Olivamidopropyl of betaines, Palmam idopropyl betaines, Palm itam idopropyl betaines, Palmitoyl Carnitine, Palm Kernelam idopropyl betaines, Polytetrafluoroethylene Acetoxypropyl of betaines, Ricinoleam idopropyl betaines, Sesam idopropyl betaines, Soyam idopropyl betaines, Stearam idopropyl betaines, Stearyl of betaines, Tallowam idopropyl betaines, Tallowam idopropyl Hydroxysultaine, Tallow of betaines, Tallow Dihydroxyethyl of betaines, Undecylenam idopropyl betaines and Wheat Germam idopropyl betaines.

A preferred betaine is, for example, Cocoamidopropylbetaine.

Soil Release Polymer

The most preferred soil release polymers are the water soluble/miscible or dispersible polyesters such as: linear polyesters sold under the Repel-O-Tex brand by Solvay, lightly branched polyesters sold under the Texcare brand by Clariant, especially Texcare SRN 170, and heavily branched polyesters such as those available from Sasol.

The polymeric soil release agents which may be used in the formulation of the present invention may include those soil release agents having:

(a) one or more nonionic hydrophilic components consisting essentially of:

polyoxyethylene segments with a degree of polymerization of at least 2, or oxypropylene or polyoxypropylene segments with a degree of polymerization of from 2 to 10, wherein said hydrophile segment does not encompass any oxypropylene unit unless it is bonded to adjacent moieties at each end by ether linkages, or a mixture of oxyalkylene units comprising oxyethylene and from 1 to 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least 25% oxyethylene units and more preferably, especially for such components having 20 to 30 oxypropylene units, at least 50% oxyethylene units; or (b) one or more hydrophobe components comprising:

(i) C3 oxyalkylene terephthalate segments, wherein, if said hydrophobe components also comprise oxyethylene terephthalate, the ratio of oxyethylene terephthalate:C3 oxyalkylene terephthalate units is 2:1 or lower, (ii) C4-C6 alkylene or oxy C4-C6 alkylene segments, or mixtures therein, (iii) poly (vinyl ester) segments, preferably polyvinyl acetate), having a degree of polymerization of at least 2, or (iv) Ci-C4 alkyl ether or C4 hydroxyalkyi ether substituents, or mixtures therein, wherein said substituents are present in the form of C1-C4 alkyl ether or C4 hydroxyalkyi ether cellulose derivatives, or mixtures therein, and such cellulose derivatives are amphiphilic, whereby they have a sufficient level of C1-C4 alkyl ether and/or C4 hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a) (i) will have a degree of polymerization of from 200, although higher levels can be used, preferably from 3 to 150, more preferably from 6 to 100.

Suitable oxy C4-C6 alkylene hydrophobe segments include, but are not limited to: end-caps of polymeric soil release agents such as MO3S(CH2)n OCH2CH2O—, where M is sodium and n is an integer from 4-6.

Soil release agents characterized by poly (vinyl ester) hydrophobe segments include: graft copolymers of poly (vinyl ester), for example, C1-C6 vinyl esters, preferably polyvinyl acetate) grafted onto polyalkylene oxide backbones, such as polyethylene oxide backbones, as described in EP 0 219 048. Commercially available soil release agents of this kind include the SOKALAN type of material, e.g., SOKALAN HP-22 available from BASF.

One type of preferred soil release agent is a copolymer having random blocks of ethylene terephthalate and polyethylene oxide (PEO) terephthalate. The molecular weight of this polymeric soil release agent is in the range of from about 25,000 to about 55,000.

Another preferred polymeric soil release agent is a polyester with repeat units of ethylene terephthalate units contains 10 to 15% by weight of ethylene terephthalate units together with 80 to 90% by weight of polyoxyethylene terephthalate units, derived from a polyoxyethylene glycol of average molecular weight 300-5,000.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. Other suitable polymeric soil release agents include the terephthalate polyesters described in U.S. Pat. No. 4,711,730, the anionic end-capped oligomeric esters described in U.S. Pat. No. 4,721,580, and the block polyester oligomeric compounds described in U.S. Pat. No. 4,702,857.

Preferred polymeric soil release agents also include the soil release agents of U.S. Pat. No. 4,877,896, which discloses anionic, especially sulfoarolyl, end-capped terephthalate esters.

The soil release agents will generally comprise from about 0.01% to about 10.0%, by weight, of the detergent formulation. Typically the soil release agents will generally comprise greater than or equal to 0.2 wt % of the detergent formulation.

In addition, for improved compatibility with detergent formulations and improved resistance to hydrolysis during storage in alkaline aqueous compositions, a nonionic polyester soil release polymer may be used of structure (I)

E-M-L-E, (I)

where the midblock M is connected to a generally hydrophilic end block E and blocks E each comprise capped oligomers of polyethylene glycol remote from the midblock, with at least 10 EO (ethylene oxide) repeat units, the end blocks being free from ester bonds, either directly or via linking moiety L which comprises the motif:

B—Ar—B where B is selected from ester moieties and Ar is 1,4 phenylene, and midblock M comprises the motif:

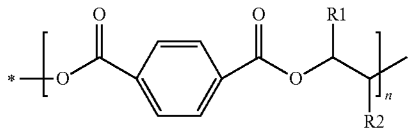

wherein R1 and R2 may be the same or different and are selected from: C1-C4 alkyl, C1-C4 alkoxy and hydrogen, provided that R1 and R2 may not both be hydrogen, n is at least 2, preferably more than 5, the ester bonds may be formed the other way around (not shown), if they are so reversed then all of them will be so reversed as described in WO2012/104159.

Methods of Making the Composition

The present disclosure relates to methods of making the compositions described herein. The compositions of the invention may be solid (for example granules or tablets) or liquid form. Preferably the compositions are in liquid form. They may be made by any process chosen by the formulator, including by a batch process, a continuous loop process, or combinations thereof.

When in the form of a liquid, the compositions of the invention may be aqueous (typically above 2 wt % or even above 5 or 10 wt % total water, up to 90 or up to 80 wt % or 70 wt % total water) or non-aqueous (typically below 2 wt % total water content). Typically the compositions of the invention will be in the form of an aqueous solution or uniform dispersion or suspension of optical brightener, DTI and optional additional adjunct materials, some of which may normally be in solid form, that have been combined with the normally liquid components of the composition, such as the liquid alcohol ethoxylate nonionic, the aqueous liquid carrier, and any other normally liquid optional ingredients. Such a solution, dispersion or suspension will be acceptably phase stable. When in the form of a liquid, the detergents of the invention preferably have viscosity from 1 to 1500 centipoises (1-1500 mPa*s), more preferably from 100 to 1000 centipoises (100-1000 mPa*s), and most preferably from 200 to 500 centipoises (200-500 mPa*s) at 20 s-1 and 21° C. Viscosity can be determined by conventional methods. Viscosity may be measured using an AR 550 rheometer from TA instruments using a plate steel spindle at 40 mm diameter and a gap size of 500 μm. The high shear viscosity at 20 s-1 and low shear viscosity at 0.05-1 can be obtained from a logarithmic shear rate sweep from 0.1-1 to 25-1 in 3 minutes time at 21 C. The preferred rheology described therein may be achieved using internal existing structuring with detergent ingredients or by employing an external rheology modifier. More preferably the detergents, such as detergent liquid compositions have a high shear rate viscosity of from about 100 centipoise to 1500 centipoise, more preferably from 100 to 1000 cps. Unit Dose detergents, such as detergent liquid compositions have high shear rate viscosity of from 400 to 1000 cps. Detergents such as laundry softening compositions typically have high shear rate viscosity of from 10 to 1000, more preferably from 10 to 800 cps, most preferably from 10 to 500 cps. Hand dishwashing compositions have high shear rate viscosity of from 300 to 4000 cps, more preferably 300 to 1000 cps.

The cleaning and/or treatment compositions in the form of a liquid herein can be prepared by combining the components thereof in any convenient order and by mixing, e.g., agitating, the resulting component combination to form a phase stable liquid detergent composition. In a process for preparing such compositions, a liquid matrix is formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactants and the solid form ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme granulates, are incorporated. As a variation of the composition preparation procedure hereinbefore described, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The adjunct ingredients in the compositions of this invention may be incorporated into the composition as the product of the synthesis generating such components, either with or without an intermediate purification step. Where there is no purification step, commonly the mixture used will comprise the desired component or mixtures thereof (and percentages given herein relate to the weight percent of the component itself unless otherwise specified) and in addition unreacted starting materials and impurities formed from side reactions and/or incomplete reaction. For example, for an ethoxylated or substituted component, the mixture will likely comprise different degrees of ethoxylation/substitution.

Method of Use

The present disclosure relates to methods of using the cleaning compositions of the present disclosure to clean a surface, such as a textile. In general, the method includes mixing the cleaning composition as described herein with water to form an aqueous liquor and contacting a surface, preferably a textile, with the aqueous liquor in a laundering step. The target surface may include a greasy soil.

The compositions of this invention, typically prepared as hereinbefore described, can be used to form aqueous washing/treatment solutions for use in the laundering/treatment of fabrics and/or hard surfaces. Generally, an effective amount of such a composition is added to water, for example in a conventional fabric automatic washing machine, to form such aqueous laundering solutions. The aqueous washing solution so formed is then contacted, typically under agitation, with the fabrics to be laundered/treated therewith. An effective amount of the detergent composition herein added to water to form aqueous laundering solutions can comprise amounts sufficient to form from about 500 to 25,000 ppm, or from 500 to 15,000 ppm of composition in aqueous washing solution, or from about 1,000 to 3,000 ppm of the detergent compositions herein will be provided in aqueous washing solution.

Typically, the wash liquor is formed by contacting the detergent with wash water in such an amount so that the concentration of the detergent in the wash liquor is from above 0 g/l to 5 g/l, or from 1 g/l, and to 4.5 g/l, or to 4.0 g/l, or to 3.5 g/l, or to 3.0 g/l, or to 2.5 g/l, or even to 2.0 g/l, or even to 1.5 g/l. The method of laundering fabric or textile may be carried out in a top-loading or front-loading automatic washing machine, or can be used in a hand-wash laundry application. In these applications, the wash liquor formed and concentration of laundry detergent composition in the wash liquor is that of the main wash cycle. Any input of water during any optional rinsing step(s) is not included when determining the volume of the wash liquor.

The wash liquor may comprise 40 liters or less of water, or 30 liters or less, or 20 liters or less, or 10 liters or less, or 8 liters or less, or even 6 liters or less of water. The wash liquor may comprise from above 0 to 15 liters, or from 2 liters, and to 12 liters, or even to 8 liters of water. Typically from 0.01 kg to 2 kg of fabric per liter of wash liquor is dosed into said wash liquor. Typically from 0.01 kg, or from 0.05 kg, or from 0.07 kg, or from 0.10 kg, or from 0.15 kg, or from 0.20 kg, or from 0.25 kg fabric per liter of wash liquor is dosed into said wash liquor. Optionally, 50 g or less, or 45 g or less, or 40 g or less, or 35 g or less, or 30 g or less, or 25 g or less, or 20 g or less, or even 15 g or less, or even 10 g or less of the composition is contacted to water to form the wash liquor. Such compositions are typically employed at concentrations of from about 500 ppm to about 15,000 ppm in solution. When the wash solvent is water, the water temperature typically ranges from about 5° C. to about 90° C. and, when the situs comprises a fabric, the water to fabric ratio is typically from about 1:1 to about 30:1. Typically the wash liquor comprising the detergent of the invention has a pH of from 3 to 11.5.

In one aspect, such method comprises the steps of optionally washing and/or rinsing said surface or fabric, contacting said surface or fabric with any composition disclosed in this specification then optionally washing and/or rinsing said surface or fabric is disclosed, with an optional drying step.

Drying of such surfaces or fabrics may be accomplished by any one of the common means employed either in domestic or industrial settings: machine drying or open-air drying. The fabric may comprise any fabric capable of being laundered in normal consumer or institutional use conditions, and the invention is particularly suitable for synthetic textiles such as polyester and nylon and especially for treatment of mixed fabrics and/or fibres comprising synthetic and cellulosic fabrics and/or fibres. As examples of synthetic fabrics are polyester, nylon, these may be present in mixtures with cellulosic fibres, for example, polycotton fabrics. The solution typically has a pH of from 7 to 11, more usually 8 to 10.5. The compositions are typically employed at concentrations from 500 ppm to 5,000 ppm in solution. The water temperatures typically range from about 5° C. to about 90° C. The water to fabric ratio is typically from about 1:1 to about 30:1.

Use of an Extracellular-Polymer-Degrading Enzyme

The present disclosure further relates to a use of an extracellular-polymer-degrading enzyme as described herein, in a cleaning composition to enhance the stain-removal and/or malodor-reducing benefits of a nuclease enzyme. The extracellular-polymer-degrading enzyme may be selected from the group consisting of: (i) a microbial endo-beta-1,6-galactanase; (ii) a mannanase with greater than about 60% identity to SEQ. ID NO. 9 (*Ascobolus stictoideus*); (iii) a mannanase with greater than about 60% identity to SEQ. ID NO. 10 (*Chaetomium virescens*); (iv) a TY145 protease with greater than about 63% identity to SEQ. ID NO. 11; (v) a PcuAmyl α-amylase with greater than about 60% identity to SEQ. ID NO. 13; and (vi) combinations thereof. The relative identities may be any percentage of identity, respectively, listed herein.

Combinations

Specifically contemplated combinations of the disclosure are herein described in the following numbered paragraphs. These combinations are intended to be illustrative in nature and are not intended to be limiting.

A. A cleaning composition comprising an enzyme system, the enzyme system comprising: (a) a nuclease enzyme; (b) an extracellular-polymer-degrading enzyme selected from the group consisting of: (i) a microbial endo-beta-1,6-galactanase; (ii) a mannanase with greater than about 60% identity to SEQ. ID NO. 9 (*Ascobolus stictoideus*); (iii) a mannanase with greater than about 60% identity to SEQ. ID NO. 10 (*Chaetomium virescens*); (iv) a TY145 protease with greater than about 63% identity to SEQ. ID NO. 11; (v) a PcuAmyl α-amylase with greater than about 60% identity to SEQ. ID NO. 13; and (vi) combinations thereof; and (c) a cleaning adjunct.

B. A cleaning composition according to paragraph A, wherein the nuclease enzyme is a deoxyribonuclease enzyme, a ribonuclease enzyme, or a mixture thereof.

C. A cleaning composition according to any of paragraphs A-B, wherein the nuclease enzyme is selected from any of E.C. classes E.C. 3.1.21.x (where x=1, 2, 3, 4, 5, 6, 7, 8, 9), 3.1.22.y (where y=1, 2, 4, 5), E.C. 3.1.30.z (where z=1, 2) or E.C. 3.1.31.1, or mixtures thereof, preferably from E.C. 3.1.21, preferably E.C. 3.1.21.1.

D. A cleaning composition according to any of paragraphs A-C, wherein the nuclease enzyme comprises a deoxyribonuclease enzyme.

E. A cleaning composition according to any of paragraphs A-D, wherein the enzyme comprises an enzyme having both RNase and DNase activity, preferably being from E.C. 3.1.30.2.

F. A cleaning composition according to any of paragraphs A-E, wherein the nuclease enzyme is a microbial enzyme, preferably a bacterial enzyme.

G. A cleaning composition according to any of paragraphs A-F, wherein the enzyme has an amino acid sequence having at least 85%, or at least 90 or at least 95% or even 100% identity with the amino acid sequence shown in SEQ ID NO:1, SEQ ID NO:2 or SEQ ID NO:3.

H. A cleaning composition according to any of paragraphs A-G, wherein the composition further comprises a β-N-acetylglucosaminidase enzyme from E.C. 3.2.1.52, preferably an enzyme having at least 70% identity to SEQ ID NO:4.

I. A cleaning composition according to any of paragraphs A-H, wherein the enzyme system comprises an endo-beta-1,6-galactanase is a fungal endo-beta-1,6-galactanase.

J. A cleaning composition according to any of paragraphs A-I, where the endo-beta-1,6-galactanase is a fungal endo-beta-1,6-galactanase.

K. A cleaning composition according to any of paragraphs A-J, wherein the endo-beta-1,6-galactanase is obtainable from *Trichoderma harzianum.*

L. A cleaning composition according to any of paragraphs A-K, wherein the endo-beta-1,6-galactanase has greater than 60% or 70% or 75% or 80% or 85% or 90% or 95%, 96%, 97%, 98%, 99%, or even 100% identity to SEQ ID NO. 7 (*Streptomyces davawensis*).

M. A cleaning composition according to any of paragraphs A-L, wherein the endo-beta-1,6-galactanase has greater than 60% or 70% or 75% or 80% or 85% or 90% or 95%, 96%, 97%, 98%, 99%, or even 100% identity to SEQ ID NO. 8 (*Trichoderma harzianum* DNase).

N. A cleaning composition according to any of paragraphs A-M, wherein the enzyme system comprises a mannanase having greater than about 60% or 70% or 75% or 80% or 85% or 90% or 95%, 96%, 97%, 98%, 99%, or even 100% identity to SEQ. ID NO. 9 (*Ascobolus stictoideus*) or a mannanase having greater than about 60% or 70% or 75% or 80% or 85% or 90% or 95%, 96%, 97%, 98%, 99%, or even 100% identity to SEQ. ID NO. 10 (*Chaetomium virescens*).

O. A cleaning composition according to any of paragraphs A-N, wherein the mannanase has greater than about 60% or 70% or 75% or 80% or 85% or 90% or 95%, 96%, 97%, 98%, 99%, or even 100% identity to SEQ. ID NO. 9 (*Ascobolus stictoideus*).

P. A cleaning composition according to any of paragraphs A-O, wherein the mannanase has greater than about 60% or 70% or 75% or 80% or 85% or 90% or 95%, 96%, 97%, 98%, 99%, or even 100% identity to SEQ. ID NO. 10 (*Chaetomium virescens*).

Q. A cleaning composition according to any of paragraphs A-P, wherein the enzyme system comprises a TY145 protease with at least 63%, at least 65%, at least 70%, at least 74%, at least 80%, at least 83%, at least 90%, at least 91%, at least 92%, at least 93%, at least 94%, at least 95%, at least 96%, at least 97%, at least 98% or at least 99% identity to SEQ. ID NO. 11.

R. A cleaning composition according to any of paragraphs A-Q, wherein the enzyme system comprises a PcuAmyl α-amylase having at least 60%, at least 65%, at least 70%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98% or even at least 99% amino acid sequence identity to SEQ. ID NO. 13.

S. A cleaning composition according to any of paragraphs A-R, wherein the enzyme system comprises additional enzymes selected from a protease, an amylase, a lipase, or combinations thereof.

T. A cleaning composition according to any of paragraphs A-S, wherein the cleaning adjunct comprises from about 1% to about 80%, by weight of the cleaning composition, of a surfactant system.

U. A cleaning composition according to any of paragraphs A-T, wherein the surfactant system comprises an anionic surfactant, preferably selected from the group consisting of alkyl sulfate, alkyl alkoxy sulfate, alkyl benzene sulfonate, paraffin sulfonate, and mixtures thereof.

V. A method of cleaning a surface, preferably a textile, comprising mixing the cleaning composition according to any of paragraphs A-U with water to form an aqueous liquor and contacting a surface, preferably a textile, with the aqueous liquor in a laundering step.

W. The use of an extracellular-polymer-degrading enzyme in a cleaning composition to enhance the stain-removal and/or malodor-reducing benefits of a nuclease enzyme, preferably an extracellular-polymer-degrading enzyme selected from the group consisting of: (i) a microbial endo-beta-1,6-galactanase; (ii) a mannanase with greater than about 60% identity to SEQ. ID NO. 9 (*Ascobolus stictoideus*); (iii) a mannanase with greater than about 60% identity to SEQ. ID NO. 10 (*Chaetomium virescens*); (iv) a TY145 protease with greater than about 63% identity to SEQ. ID NO. 11; (v) a PcuAmyl α-amylase with greater than about 60% identity to SEQ. ID NO. 13; and (vi) combinations thereof.

EXAMPLES

The following are illustrative examples of cleaning compositions of the invention and are not intended to be limiting.

Examples 1-7: Heavy Duty Liquid Laundry Detergent Compositions

| Ingredients | 1 | 2 | 3 | 4<br>% weight | 5 | 6 | 7 |
|---|---|---|---|---|---|---|---|
| AES | 6.77 | 5.16 | 5.36 | 1.30 | 0.45 | — | — |
| LAS | 0.86 | 2.06 | 2.72 | 0.68 | 0.95 | 1.56 | 3.55 |
| HSAS | 1.85 | 2.63 | 2.02 | — | — | — | — |
| Ethoxylated (7-9) alcohol | 6.32 | 9.85 | 10.20 | 7.92 | 8.40 | 12.44 | 35.45 |
| $C_{12-14}$ dimethyl Amine Oxide | 0.30 | 0.73 | 0.23 | 0.37 | — | — | — |
| $C_{12-18}$ Fatty Acid | 0.80 | 1.90 | 0.60 | 0.99 | 1.20 | — | 15.00 |
| Citric Acid | 2.50 | 3.96 | 1.88 | 1.98 | 0.90 | 2.50 | 0.60 |
| Optical Brightener 1 | 1.00 | 0.80 | 0.10 | 0.30 | 0.05 | 0.50 | 0.001 |
| Optical Brightener 3 | 0.001 | 0.05 | 0.01 | 0.20 | 0.50 | — | 1.00 |
| Sodium formate | 1.60 | 0.09 | 1.20 | 0.04 | 1.60 | 1.20 | 0.20 |
| DTI 1 | 0.32 | 0.05 | — | 0.60 | 0.10 | 0.60 | 0.01 |
| DTI 2 | 0.32 | 0.10 | 0.60 | 0.60 | 0.05 | 0.40 | 0.20 |
| Sodium hydroxide | 2.30 | 3.80 | 1.70 | 1.90 | 1.70 | 2.50 | 2.30 |
| Monoethanolamine | 1.40 | 1.49 | 1.00 | 0.70 | — | — | — |
| Diethylene glycol | 5.50 | — | 4.10 | — | — | — | — |
| Chelant 1 | 0.15 | 0.15 | 0.11 | 0.07 | 0.50 | 0.11 | 0.80 |
| 4-formyl-phenylboronic acid | — | — | — | — | 0.05 | 0.02 | 0.01 |
| Sodium tetraborate | 1.43 | 1.50 | 1.10 | 0.75 | — | 1.07 | — |
| Ethanol | 1.54 | 1.77 | 1.15 | 0.89 | — | 3.00 | 7.00 |
| Polymer 1 | 0.10 | — | — | — | — | — | 2.00 |
| Polymer 2 | 0.30 | 0.33 | 0.23 | 0.17 | — | — | — |
| Polymer 3 | — | — | — | — | — | — | 0.80 |
| Polymer 4 | 0.80 | 0.81 | 0.60 | 0.40 | 1.00 | 1.00 | — |
| 1,2-Propanediol | — | 6.60 | — | 3.30 | 0.50 | 2.00 | 8.00 |
| Structurant | 0.10 | — | — | — | — | — | 0.10 |
| Perfume | 1.60 | 1.10 | 1.00 | 0.80 | 0.90 | 1.50 | 1.60 |
| Perfume encapsulate | 0.10 | 0.05 | 0.01 | 0.02 | 0.10 | 0.05 | 0.10 |
| Protease | 0.80 | 0.8 | 0.70 | 0.90 | 0.70 | 0.60 | 0.80 |
| Amylase | 0.30 | 0.3 | | 0.10 | — | 0.40 | 0.30 |
| Lipase | 0.40 | | 0.30 | 0.10 | 0.20 | — | 0.40 |
| Mannanase | 0.5 | 0.03 | 0.01 | 0.05 | 0.03 | 0.01 | 0.003 |
| Galactanase | 0.5 | 0.03 | 0.01 | 0.05 | 0.03 | 0.01 | 0.003 |
| Nuclease | 0.03 | 0.03 | 0.03 | 0.03 | 0.03 | 0.03 | 0.003 |
| Dispersin B | — | — | — | 0.05 | 0.03 | 0.001 | 0.001 |
| Acid Violet 50 | 0.05 | — | — | — | — | — | 0.005 |
| Direct Violet 9 | — | — | — | — | — | 0.05 | — |
| Violet DD | — | 0.035 | 0.02 | 0.037 | 0.04 | — | — |
| Water, dyes & minors | | | | Balance | | | |
| pH | | | | 8.2 | | | |

Based on total cleaning and/or treatment composition weight. Enzyme levels are reported as raw material.

Examples 8 to 18: Unit Dose Compositions

These examples provide various formulations for unit dose laundry detergents. Compositions 8 to 12 comprise a single unit dose compartment. The film used to encapsulate the compositions is a polyvinyl-alcohol-based film.

| Ingredients | 8 | 9 | 10 | 11 | 12 |
|---|---|---|---|---|---|
| | % weight | | | | |
| LAS | 19.09 | 16.76 | 8.59 | 6.56 | 3.44 |
| AES | 1.91 | 0.74 | 0.18 | 0.46 | 0.07 |
| Ethoxylated (7) alcohol | 14.00 | 17.50 | 26.33 | 28.08 | 31.59 |
| Citric Acid | 0.6 | 0.6 | 0.6 | 0.6 | 0.6 |
| C12-15 Fatty Acid | 14.8 | 14.8 | 14.8 | 14.8 | 14.8 |
| Polymer 3 | 4.0 | 4.0 | 4.0 | 4.0 | 4.0 |
| Chelant 2 | 1.2 | 1.2 | 1.2 | 1.2 | 1.2 |
| Optical Brightener 1 | 0.20 | 0.25 | 0.01 | 0.01 | 0.50 |
| Optical Brightener 2 | 0.20 | — | 0.25 | 0.03 | 0.01 |
| Optical Brightener 3 | 0.18 | 0.09 | 0.30 | 0.01 | — |
| DTI 1 | 0.10 | — | 0.20 | 0.01 | 0.05 |
| DTI 2 | — | 0.10 | 0.20 | 0.25 | 0.05 |
| Glycerol | 6.1 | 6.1 | 6.1 | 6.1 | 6.1 |
| Monoethanol amine | 8.0 | 8.0 | 8.0 | 8.0 | 8.0 |
| Tri-isopropanol amine | — | — | 2.0 | — | — |
| Tri-ethanol amine | — | 2.0 | — | — | — |
| Cumene sulfonate | — | — | — | — | 2.0 |
| Protease | 0.80 | 0.60 | 0.07 | 1.00 | 1.50 |
| Amylase | 0.07 | 0.05 | — | 0.10 | 0.01 |
| Lipase | 0.20 | — | 0.30 | 0.50 | 0.05 |

-continued

| Ingredients | 8 | 9 | 10 | 11 | 12 |
|---|---|---|---|---|---|
| | % weight | | | | |
| Mannanase | 0.5 | 0.05 | 0.005 | 0.05 | 0.005 |
| Galactanase | 0.5 | 0.05 | 0.005 | 0.05 | 0.005 |
| Nuclease | 0.005 | 0.05 | 0.005 | 0.010 | 0.005 |
| Dispersin B | 0.010 | 0.05 | 0.005 | 0.005 | — |
| Cyclohexyl dimethanol | — | — | — | 2.0 | — |
| Acid violet 50 | 0.03 | 0.02 | | | |
| Violet DD | | | 0.01 | 0.05 | 0.02 |
| Structurant | 0.14 | 0.14 | 0.14 | 0.14 | 0.14 |
| Perfume | 1.9 | 1.9 | 1.9 | 1.9 | 1.9 |
| Water and miscellaneous | | | To 100% | | |
| pH | | | 7.5-8.2 | | |

Based on total cleaning and/or treatment composition weight. Enzyme levels are reported as raw material.

In the following examples the unit dose has three compartments, but similar compositions can be made with two, four or five compartments. The film used to encapsulate the compartments is polyvinyl alcohol.

| Ingredients | Base compositions | | | |
|---|---|---|---|---|
| | 13 | 14 | 15 | 16 |
| | % weight | | | |
| HLAS | 26.82 | 16.35 | 7.50 | 3.34 |
| Ethoxylated (7) alcohol | 17.88 | 16.35 | 22.50 | 30.06 |
| Citric Acid | 0.5 | 0.7 | 0.6 | 0.5 |
| C12-15 Fatty acid | 16.4 | 6.0 | 11.0 | 13.0 |
| Polymer 1 | 2.9 | 0.1 | — | — |
| Polymer 3 | 1.1 | 5.1 | 2.5 | 4.2 |
| Cationic cellulose polymer | — | — | 0.3 | 0.5 |
| Polymer 6 | — | 1.5 | 0.3 | 0.2 |
| Chelant 2 | 1.1 | 2.0 | 0.6 | 1.5 |
| Optical Brightener 1 | 0.20 | 0.25 | 0.01 | 0.005 |
| Optical Brightener 3 | 0.18 | 0.09 | 0.30 | 0.005 |
| DTI 1 | 0.1 | — | 0.2 | — |
| DTI 2 | — | 0.1 | 0.2 | — |
| Glycerol | 5.3 | 5.0 | 5.0 | 4.2 |
| Monoethanolamine | 10.0 | 8.1 | 8.4 | 7.6 |
| Polyethyleneglycol | — | — | 2.5 | 3.0 |
| Potassium sulfite | 0.2 | 0.3 | 0.5 | 0.7 |
| Protease | 0.80 | 0.60 | 0.80 | 0.80 |
| Amylase | 0.20 | 0.20 | — | 0.30 |
| Mannanase | 0.5 | 0.01 | 0.005 | 0.005 |
| Galactanase | 0.5 | 0.01 | 0.005 | 0.005 |
| Nuclease | 0.05 | 0.01 | 0.005 | 0.005 |
| Dispersin B | — | 0.010 | 0.010 | 0.010 |
| $MgCl_2$ | 0.2 | 0.2 | 0.1 | 0.3 |
| Structurant | 0.2 | 0.1 | 0.2 | 0.2 |
| Acid Violet 50 | 0.04 | 0.03 | 0.05 | 0.03 |
| Perfume/encapsulates | 0.10 | 0.30 | 0.01 | 0.05 |
| Solvents and misc. | | To 100% | | |
| pH | | 7.0-8.2 | | |

| Ingredients | Finishing compositions | | | | | |
|---|---|---|---|---|---|---|
| | 17 | | | 18 | | |
| | Compartment | | | | | |
| | A | B | C | A | B | C |
| | Volume of each compartment | | | | | |
| | 40 ml | 5 ml | 5 ml | 40 ml | 5 ml | 5 ml |
| | Active material in Wt. % | | | | | |
| Lipase | 0 | 0.01 | 0 | 0 | 0.01 | 0 |
| Perfume | 1.6 | 1.6 | 1.6 | 1.6 | 1.6 | 1.6 |
| Violet DD | 0 | 0.006 | 0 | 0 | 0.004 | — |
| TiO2 | — | — | 0.1 | — | | 0.1 |
| Sodium Sulfite | 0.4 | 0.4 | 0.4 | 0.3 | 0.3 | 0.3 |

-continued

| | | | | | | |
|---|---|---|---|---|---|---|
| Polymer 5 | — | | | 2 | — | — |
| Hydrogenated castor oil | 0.14 | 0.14 | 0.14 | 0.14 | 0.14 | 0.14 |
| Base Composition 13, 14, 15 or 16 | | | Add to 100% | | | |

Based on total cleaning and/or treatment composition weight, enzyme levels are reported as raw material.

Examples 19 to 24: Granular Laundry Detergent Compositions for Hand Washing or Washing Machines, Typically Top-Loading Washing Machines

| Ingredient | 19 | 20 | 21 | 22 | 23 | 24 |
|---|---|---|---|---|---|---|
| | | | % weight | | | |
| LAS | 11.33 | 10.81 | 8.04 | 8.20 | 3.92 | 2.29 |
| Quaternary ammonium | 0.70 | 0.20 | 1.00 | 0.60 | — | — |
| AES | 0.51 | 0.49 | 0.32 | — | 0.08 | 0.10 |
| Ethoxylated (7) alcohol | 2.00 | 1.50 | 12.54 | 11.20 | 16.00 | 21.51 |
| Sodium Tripolyphosphate | 5.0 | — | 4.0 | 9.0 | 2.0 | — |
| Zeolite A | — | 1.0 | — | 1.0 | 4.0 | 1.0 |
| Sodium silicate 1.6R | 7.0 | 5.0 | 2.0 | 3.0 | 3.0 | 5.0 |
| Sodium carbonate | 20.0 | 17.0 | 23.0 | 14.0 | 14.0 | 16.0 |
| Polyacrylate MW 4500 | 1.0 | 0.6 | 1.0 | 1.0 | 1.5 | 1.0 |
| Polymer 6 | 0.1 | 0.2 | — | — | 0.1 | — |
| Carboxymethyl cellulose | 1.0 | 0.3 | 1.0 | 1.0 | 1.0 | 1.0 |
| Acid Violet 50 | 0.05 | — | 0.02 | — | 0.04 | — |
| Violet DD | — | 0.03 | — | 0.03 | — | 0.03 |
| Protease | 0.10 | 0.10 | 0.10 | 0.10 | 0.10 | 0.10 |
| Amylase | 0.03 | 0.03 | 0.03 | 0.03 | 0.03 | 0.03 |
| Mannanase | 0.10 | 0.01 | 0.01 | 0.001 | 0.001 | 0.01 |
| Galactanase | 0.10 | 0.01 | 0.01 | 0.001 | 0.001 | 0.01 |
| Nuclease | 0.001 | 0.001 | 0.01 | 0.001 | 0.001 | 0.01 |
| Dispersin B | 0.001 | 0.001 | 0.05 | — | 0.001 | — |
| Optical Brightener 1 | 0.200 | 0.001 | 0.300 | 0.650 | 0.050 | 0.001 |
| Optical Brightener 2 | 0.060 | — | 0.650 | 0.180 | 0.200 | 0.060 |
| Optical Brightener 3 | 0.100 | 0.060 | 0.050 | — | 0.030 | 0.300 |
| Chelant 1 | 0.60 | 0.80 | 0.60 | 0.25 | 0.60 | 0.60 |
| DTI 1 | 0.32 | 0.15 | 0.15 | — | 0.10 | 0.10 |
| DTI 2 | 0.32 | 0.15 | 0.30 | 0.30 | 0.10 | 0.20 |
| Sodium Percarbonate | — | 5.2 | 0.1 | — | — | — |
| Sodium Perborate | 4.4 | — | 3.85 | 2.09 | 0.78 | 3.63 |
| Nonanoyloxybenzensulfonate | 1.9 | 0.0 | 1.66 | 0.0 | 0.33 | 0.75 |
| Tetraacetylehtylenediamine | 0.58 | 1.2 | 0.51 | 0.0 | 0.015 | 0.28 |
| Photobleach | 0.0030 | 0.0 | 0.0012 | 0.0030 | 0.0021 | — |
| S-ACMC | 0.1 | 0.0 | 0.0 | 0.0 | 0.06 | 0.0 |
| Sulfate/Moisture | | | Balance | | | |

Examples 25-37: Granular Laundry Detergent Compositions Typically for Front-Loading Automatic Washing Machines

| Ingredient | 25 | 26 | 27 | 28 | 29 | 30 |
|---|---|---|---|---|---|---|
| | | | % weight | | | |
| LAS | 8.08 | 7.05 | 5.27 | 6.24 | 2.30 | 1.09 |
| AES | — | 0.90 | 0.21 | 0.18 | — | 0.06 |
| AS | 0.34 | — | — | — | — | — |
| Ethoxylated (7) alcohol | 2.28 | 3.95 | 5.72 | 5.98 | 9.20 | 10.35 |
| Quaternary ammonium | 0.5 | — | — | 0.3 | — | — |
| Crystalline layered silicate | 4.1 | — | 4.8 | — | — | — |
| Zeolite A | 5.0 | — | 2.0 | — | 2.0 | 2.0 |
| Citric acid | 3.0 | 4.0 | 3.0 | 4.0 | 2.5 | 3.0 |
| Sodium carbonate | 11.0 | 17.0 | 12.0 | 15.0 | 18.0 | 18.0 |
| Sodium silicate 2R | 0.08 | — | 0.11 | — | — | — |
| Optical Brightener 1 | — | 0.25 | 0.05 | 0.01 | 0.10 | 0.02 |
| Optical Brightener 2 | — | — | 0.25 | 0.20 | 0.01 | 0.08 |
| Optical Brightener 3 | — | 0.06 | 0.04 | 0.15 | — | 0.05 |
| DTI 1 | 0.08 | — | 0.04 | — | 0.10 | 0.01 |

-continued

| | | | | | | |
|---|---|---|---|---|---|---|
| DTI 2 | 0.08 | — | 0.04 | 0.10 | 0.10 | 0.02 |
| Soil release agent | 0.75 | 0.72 | 0.71 | 0.72 | — | — |
| Acrylic/maleic acid copolymer | 1.1 | 3.7 | 1.0 | 3.7 | 2.6 | 3.8 |
| Carboxymethyl cellulose | 0.2 | 1.4 | 0.2 | 1.4 | 1.0 | 0.5 |
| Protease | 0.20 | 0.20 | 0.30 | 0.15 | 0.12 | 0.13 |
| Amylase | 0.20 | 0.15 | — | 0.30 | 0.15 | 0.15 |
| Lipase | 0.05 | — | 0.10 | 0.05 | 0.05 | 0.05 |
| Mannanase | 0.2 | 0.01 | 0.02 | 0.02 | 0.01 | 0.003 |
| Galactanase | 0.2 | 0.01 | 0.02 | 0.02 | 0.01 | 0.003 |
| Nuclease | 0.002 | 0.01 | 0.02 | 0.02 | 0.01 | 0.003 |
| Dispersin B | 0.002 | 0.01 | 0.02 | 0.02 | 0.01 | 0.002 |
| Tetraacetylehtylenediamine | 3.6 | 4.0 | 3.6 | 4.0 | 2.2 | 1.4 |
| Sodium percabonate | 13.0 | 13.2 | 13.0 | 13.2 | 16.0 | 14.0 |
| Chelant 3 | — | 0.2 | — | 0.2 | — | 0.2 |
| Chelant 2 | 0.2 | — | 0.2 | — | 0.2 | 0.2 |
| $MgSO_4$ | — | 0.42 | — | 0.42 | — | 0.4 |
| Perfume | 0.5 | 0.6 | 0.5 | 0.6 | 0.6 | 0.6 |
| Suds suppressor agglomerate | 0.05 | 0.10 | 0.05 | 0.10 | 0.06 | 0.05 |
| Soap | 0.45 | 0.45 | 0.45 | 0.45 | — | — |
| Acid Violet 50 | 0.04 | — | 0.05 | — | 0.04 | — |
| Violet DD | — | 0.04 | — | 0.05 | — | 0.04 |
| S-ACMC | 0.01 | 0.01 | — | 0.01 | — | — |
| Direct Violet 9 (active) | — | — | 0.0001 | 0.0001 | — | — |
| Sulfate/Water & Miscellaneous | | | Balance | | | |

| | |
|---|---|
| AES | is $C_{12-15}$ alkyl ethoxy (1-3) sulfate |
| Amylase | as described in the present disclosure |
| AS | is $C_{12-14}$ alkylsulfate |
| Chelant 1 | is diethylene triamine pentaacetic acid |
| Chelant 2 | is 1-hydroxy ethane 1,1-diphosphonic acid |
| Chelant 3 | is sodium salt of ethylenediamine-N,N'-disuccinic acid, (S,S) isomer (EDDS) |
| Dispersin B | is a glycoside hydrolase, reported as 1000 mg active/g |
| DTI 1 | is poly(4-vinylpyridine-1-oxide) (such as Chromabond S-403E ®), |
| DTI 2 | is poly(1-vinylpyrrolidone-co-1-vinylimidazole) (such as Sokalan HP56 ®). |
| Galactanase | Endo-beta-1,6-galactanase as described in present disclosure |
| HSAS | is mid-branched alkyl sulfate as disclosed in U.S. Pat. No. 6,020,303 and U.S. Pat. No. 6,060,443 |
| LAS | is linear alkylbenzenesulfonate having an average aliphatic carbon chain length $C_9$-$C_{15}$ (HLAS is acid form). |
| Lipase | as described in present disclosure |
| Mannanase | as described in present disclosure |
| Nuclease | is a Phosphodiesterase according to SEQ ID NO 1, reported as 1000 mg active/g |
| Optical Brightener 1 | is disodium 4,4'-bis{[4-anilino-6-morpholino-s-triazin-2-yl]-amino}-2,2'-stilbenedisulfonate |
| Optical Brightener 2 | is disodium 4,4'-bis-(2-sulfostyryl)biphenyl (sodium salt) |
| Optical Brightener 3 | is Optiblanc SPL10 ® from 3V Sigma |
| Perfume encapsulate | is a core-shell melamine formaldehyde perfume microcapsules. |
| Photobleach | is a sulfonated zinc phthalocyanine |
| Polishing enzyme | is Para-nitrobenzyl esterase, reported as 1000 mg active/g |
| Polymer 1 | is bis(($C_2H_5O$)($C_2H_4O$)$n$)($CH_3$)—$N^+$—$C_xH2_x$—$N^+$—($CH_3$)—bis(($C_2H_5O$)($C_2H_4O$)$n$), wherein n = 20-30, x = 3 to 8 or sulfated or sulfonsulfonated variants thereof |
| Polymer 2 | is ethoxylated ($EO_{15}$) tetraethylene pentamine |
| Polymer 3 | is ethoxylated polyethylenimine |
| Polymer 4 | is ethoxylated hexamethylene diamine |
| Polymer 5 | is Acusol 305, provided by Rohm&Haas |
| Polymer 6 | is a polyethyleneglycol polymer grafted with vinyl acetate side chains, provided by BASF. |
| Protease | as described in present disclosure |
| Quaternary ammonium | is $C_{12-14}$ Dimethylhydroxyethyl ammonium chloride |
| S-ACMC | is Reactive Blue 19 Azo-CM-Cellulose provided by Megazyme |
| Soil release agent | is Repel-o-tex ® SF2 |
| Structurant | is Hydrogenated Castor Oil |
| Violet DD | is a thiophene azo dye provided by Milliken |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A cleaning composition comprising an enzyme system, the enzyme system comprising:

(a) a nuclease enzyme;

(b) an extracellular-polymer-degrading enzyme that is a mannanase with greater than about 90% identity to SEQ. ID NO. 10 (*Chaetomium virescens*); and (c) a cleaning adjunct.

2. A cleaning composition according to claim 1, wherein the nuclease enzyme is a deoxyribonuclease enzyme, a ribonuclease enzyme, or a mixture thereof.

3. A cleaning composition according to claim 1, wherein the nuclease enzyme is selected from any of E.C. classes E.C. 3.1.21.x (where x=1, 2, 3, 4, 5, 6, 7, 8, 9), 3.1.22.y (where y=1, 2, 4, 5), E.C. 3.1.30.z (where z=1, 2) or E.C. 3.1.31.1, or mixtures thereof.

4. A cleaning composition according to claim 1 wherein the nuclease enzyme comprises a deoxyribonuclease enzyme.

5. A cleaning composition according to claim 1 in which the nuclease enzyme comprises a nuclease enzyme having both RNase and DNase activity.

6. A cleaning composition according to claim 1, wherein the nuclease enzyme is a microbial enzyme.

7. A cleaning composition according to claim 1, wherein the nuclease enzyme has an amino acid sequence having at least 85%, or at least 90 or at least 95% or even 100% identity with the amino acid sequence shown in SEQ ID NO:1, SEQ ID NO:2 or SEQ ID NO:3.

8. A cleaning composition according to claim 1, wherein the enzyme system comprises a mannanase having greater than about 95% identity to SEQ. ID NO. 10 (*Chaetomium virescens*).

9. A cleaning composition according to claim 8, wherein the mannanase has greater than about 98% identity to SEQ. ID NO. 10 (*Chaetomium virescens*).

10. A cleaning composition according to claim 1, wherein the enzyme system comprises additional enzymes selected from a protease, an amylase, a lipase, or combinations thereof.

11. A cleaning composition according to claim 1, wherein the cleaning adjunct comprises from about 1% to about 80%, by weight of the cleaning composition, of a surfactant system.

12. A cleaning composition according to claim 10, wherein the surfactant system comprises an anionic surfactant.

13. A method of cleaning a surface, a textile, comprising mixing the cleaning composition according to claim 1 with water to form an aqueous liquor and contacting a textile with the aqueous liquor in a laundering step.

14. A cleaning composition according to claim 3, wherein the nuclease enzyme is selected from E.C. class E.C. 3.1.21.x (where x=1, 2, 3, 4, 5, 6, 7, 8, 9).

15. A cleaning composition according to claim 14, wherein the nuclease enzyme is selected from E.C. class E.C. 3.1.21.1.

16. A cleaning composition according to claim 5, wherein the nuclease enzyme having both RNase and DNase activity is from E.C. 3.1.30.2.

17. A cleaning composition according to claim 6, wherein the nuclease enzyme is a bacterial enzyme.

18. A cleaning composition according to claim 9, wherein the mannanase has greater than about 99% identity to SEQ. ID NO. 10 (*Chaetomium virescens*).

19. A cleaning composition according to claim 12, wherein the anionic surfactant comprises a member selected from the group consisting of alkyl sulfate, alkyl alkoxy sulfate, alkyl benzene sulfonate, paraffin sulfonate, and mixtures thereof.

20. A cleaning composition according to claim 19, wherein the anionic surfactant comprises a member selected from the group consisting of alkyl sulfate, alkyl alkoxy sulfate, alkyl benzene sulfonate, and mixtures thereof.

* * * * *

SEQUENCE LISTING

<160> NUMBER OF SEQ ID NOS: 14

<210> SEQ ID NO 1
<211> LENGTH: 109
<212> TYPE: PRT
<213> ORGANISM: Bacillus licheniformis

<400> SEQUENCE: 1

Ala Arg Tyr Asp Asp Val Leu Tyr Phe Pro Ala Ser Arg Tyr Pro Glu
1 5 10 15

Thr Gly Ala His Ile Ser Asp Ala Ile Lys Ala Gly His Ala Asp Val
20 25 30

Cys Thr Ile Glu Arg Ser Gly Ala Asp Lys Arg Arg Gln Glu Ser Leu
35 40 45

Lys Gly Ile Pro Thr Lys Pro Gly Phe Asp Arg Asp Glu Trp Pro Met
50 55 60

Ala Met Cys Glu Glu Gly Gly Lys Gly Ala Ser Val Arg Tyr Val Ser
65 70 75 80

Ser Ser Asp Asn Arg Gly Ala Gly Ser Trp Val Gly Asn Arg Leu Asn
85 90 95

Gly Tyr Ala Asp Gly Thr Arg Ile Leu Phe Ile Val Gln
100 105

<210> SEQ ID NO 2
<211> LENGTH: 109
<212> TYPE: PRT
<213> ORGANISM: Bacillus subtilis

<400> SEQUENCE: 2

Ala Ser Ser Tyr Asp Lys Val Leu Tyr Phe Pro Leu Ser Arg Tyr Pro
1 5 10 15

Glu Thr Gly Ser His Ile Arg Asp Ala Ile Ala Glu Gly His Pro Asp
20 25 30

Ile Cys Thr Ile Asp Asp Gly Ala Asp Lys Arg Arg Glu Glu Ser Leu
35 40 45

Lys Gly Ile Pro Thr Lys Pro Gly Tyr Asp Arg Asp Glu Trp Pro Met
50 55 60

Ala Val Cys Glu Glu Gly Gly Ala Gly Ala Asp Val Arg Tyr Val Thr
65 70 75 80

Pro Ser Asp Asn Arg Gly Ala Gly Ser Trp Val Gly Asn Gln Met Ser
85 90 95

Ser Tyr Pro Asp Gly Thr Arg Val Leu Phe Ile Val Gln
100 105

<210> SEQ ID NO 3
<211> LENGTH: 109
<212> TYPE: PRT
<213> ORGANISM: Bacillus licheniformis

<400> SEQUENCE: 3

Ala Arg Tyr Asp Asp Ile Leu Tyr Phe Pro Ala Ser Arg Tyr Pro Glu
1 5 10 15

Thr Gly Ala His Ile Ser Asp Ala Ile Lys Ala Gly His Ser Asp Val
20 25 30

Cys Thr Ile Glu Arg Ser Gly Ala Asp Lys Arg Arg Gln Glu Ser Leu
35 40 45

Lys Gly Ile Pro Thr Lys Pro Gly Phe Asp Arg Asp Glu Trp Pro Met
50 55 60

-continued

```
Ala Met Cys Glu Glu Gly Gly Lys Gly Ala Ser Val Arg Tyr Val Ser
65                  70                  75                  80

Ser Ser Asp Asn Arg Gly Ala Gly Ser Trp Val Gly Asn Arg Leu Ser
                85                  90                  95

Gly Phe Ala Asp Gly Thr Arg Ile Leu Phe Ile Val Gln
            100                 105


<210> SEQ ID NO 4
<211> LENGTH: 361
<212> TYPE: PRT
<213> ORGANISM: Aggregatibacter actinomycetemcomitans

<400> SEQUENCE: 4

Asn Cys Cys Val Lys Gly Asn Ser Ile Tyr Pro Gln Lys Thr Ser Thr
1               5                   10                  15

Lys Gln Thr Gly Leu Met Leu Asp Ile Ala Arg His Phe Tyr Ser Pro
            20                  25                  30

Glu Val Ile Lys Ser Phe Ile Asp Thr Ile Ser Leu Ser Gly Gly Asn
        35                  40                  45

Phe Leu His Leu His Phe Ser Asp His Glu Asn Tyr Ala Ile Glu Ser
    50                  55                  60

His Leu Leu Asn Gln Arg Ala Glu Asn Ala Val Gln Gly Lys Asp Gly
65                  70                  75                  80

Ile Tyr Ile Asn Pro Tyr Thr Gly Lys Pro Phe Leu Ser Tyr Arg Gln
                85                  90                  95

Leu Asp Asp Ile Lys Ala Tyr Ala Lys Ala Lys Gly Ile Glu Leu Ile
            100                 105                 110

Pro Glu Leu Asp Ser Pro Asn His Met Thr Ala Ile Phe Lys Leu Val
        115                 120                 125

Gln Lys Asp Arg Gly Val Lys Tyr Leu Gln Gly Leu Lys Ser Arg Gln
    130                 135                 140

Val Asp Asp Glu Ile Asp Ile Thr Asn Ala Asp Ser Ile Thr Phe Met
145                 150                 155                 160

Gln Ser Leu Met Ser Glu Val Ile Asp Ile Phe Gly Asp Thr Ser Gln
                165                 170                 175

His Phe His Ile Gly Gly Asp Glu Phe Gly Tyr Ser Val Glu Ser Asn
            180                 185                 190

His Glu Phe Ile Thr Tyr Ala Asn Lys Leu Ser Tyr Phe Leu Glu Lys
        195                 200                 205

Lys Gly Leu Lys Thr Arg Met Trp Asn Asp Gly Leu Ile Lys Asn Thr
    210                 215                 220

Phe Glu Gln Ile Asn Pro Asn Ile Glu Ile Thr Tyr Trp Ser Tyr Asp
225                 230                 235                 240

Gly Asp Thr Gln Asp Lys Asn Glu Ala Ala Glu Arg Arg Asp Met Arg
                245                 250                 255

Val Ser Leu Pro Glu Leu Leu Ala Lys Gly Phe Thr Val Leu Asn Tyr
            260                 265                 270

Asn Ser Tyr Tyr Leu Tyr Ile Val Pro Lys Ala Ser Pro Thr Phe Ser
        275                 280                 285

Gln Asp Ala Ala Phe Ala Ala Lys Asp Val Ile Lys Asn Trp Asp Leu
    290                 295                 300

Gly Val Trp Asp Gly Arg Asn Thr Lys Asn Arg Val Gln Asn Thr His
305                 310                 315                 320

Glu Ile Ala Gly Ala Ala Leu Ser Ile Trp Gly Glu Asp Ala Lys Ala
```

-continued

```
                325                 330                 335

Leu Lys Asp Glu Thr Ile Gln Lys Asn Thr Lys Ser Leu Leu Glu Ala
            340                 345                 350

Val Ile His Lys Thr Asn Gly Asp Glu
        355                 360


<210> SEQ ID NO 5
<211> LENGTH: 204
<212> TYPE: PRT
<213> ORGANISM: Aspergillus oryzae

<400> SEQUENCE: 5

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
            20                  25                  30

Ile Leu Cys Lys Gly Ala Pro Asn Val Leu Gln Arg Val Asn Glu Lys
        35                  40                  45

Thr Lys Asn Ser Asn Arg Asp Arg Ser Gly Ala Asn Lys Gly Pro Phe
    50                  55                  60

Lys Asp Pro Gln Lys Trp Gly Ile Lys Ala Leu Pro Pro Lys Asn Pro
65                  70                  75                  80

Ser Trp Ser Ala Gln Asp Phe Lys Ser Pro Glu Glu Tyr Ala Phe Ala
                85                  90                  95

Ser Ser Leu Gln Gly Gly Thr Asn Ala Ile Leu Ala Pro Val Asn Leu
            100                 105                 110

Ala Ser Gln Asn Ser Gln Gly Gly Val Leu Asn Gly Phe Tyr Ser Ala
        115                 120                 125

Asn Lys Val Ala Gln Phe Asp Pro Ser Lys Pro Gln Gln Thr Lys Gly
    130                 135                 140

Thr Trp Phe Gln Ile Thr Lys Phe Thr Gly Ala Ala Gly Pro Tyr Cys
145                 150                 155                 160

Lys Ala Leu Gly Ser Asn Asp Lys Ser Val Cys Asp Lys Asn Lys Asn
                165                 170                 175

Ile Ala Gly Asp Trp Gly Phe Asp Pro Ala Lys Trp Ala Tyr Gln Tyr
            180                 185                 190

Asp Glu Lys Asn Asn Lys Phe Asn Tyr Val Gly Lys
        195                 200


<210> SEQ ID NO 6
<211> LENGTH: 188
<212> TYPE: PRT
<213> ORGANISM: Trichoderma harzianum

<400> SEQUENCE: 6

Ala Pro Ala Pro Met Pro Thr Pro Pro Gly Ile Pro Thr Glu Ser Ser
1               5                   10                  15

Ala Arg Thr Gln Leu Ala Gly Leu Thr Val Ala Val Ala Gly Ser Gly
            20                  25                  30

Thr Gly Tyr Ser Arg Asp Leu Phe Pro Thr Trp Asp Ala Ile Ser Gly
        35                  40                  45

Asn Cys Asn Ala Arg Glu Tyr Val Leu Lys Arg Asp Gly Glu Gly Val
    50                  55                  60

Gln Val Asn Asn Ala Cys Glu Ser Gln Ser Gly Thr Trp Ile Ser Pro
65                  70                  75                  80

Tyr Asp Asn Ala Ser Phe Thr Asn Ala Ser Ser Leu Asp Ile Asp His
```

-continued

```
                85                  90                  95

Met Val Pro Leu Lys Asn Ala Trp Ile Ser Gly Ala Ser Ser Trp Thr
            100                 105                 110

Thr Ala Gln Arg Glu Ala Leu Ala Asn Asp Val Ser Arg Pro Gln Leu
        115                 120                 125

Trp Ala Val Ser Ala Ser Ala Asn Arg Ser Lys Gly Asp Arg Ser Pro
    130                 135                 140

Asp Gln Trp Lys Pro Pro Leu Thr Ser Phe Tyr Cys Thr Tyr Ala Lys
145                 150                 155                 160

Ser Trp Ile Asp Val Lys Ser Phe Tyr Lys Leu Thr Ile Thr Ser Ala
                165                 170                 175

Glu Lys Thr Ala Leu Ser Ser Met Leu Asp Thr Cys
            180                 185


<210> SEQ ID NO 7
<211> LENGTH: 463
<212> TYPE: PRT
<213> ORGANISM: Streptomyces davawensis

<400> SEQUENCE: 7

Asp Ala Thr Ile Val Ile Asn Pro Gly Thr Arg Tyr Gly Thr Trp Glu
1               5                   10                  15

Gly Trp Gly Thr Ser Leu Ala Trp Trp Gly Asn Val Phe Gly Thr Arg
            20                  25                  30

Asp Asp Phe Ala Asp Leu Phe Phe Thr Thr Lys Ser Val Thr Tyr Asn
        35                  40                  45

Gly Thr Ser Leu Pro Gly Leu Gly Leu Asn Ile Ala Arg Tyr Asn Leu
    50                  55                  60

Gly Ala Cys Ser Trp Asn Ala Val Asn Gly Glu Thr Met Val Lys Ser
65                  70                  75                  80

Pro Asn Ile Pro Ala Phe Lys Gln Ile Glu Gly Phe Trp Gln Asp Trp
                85                  90                  95

Asn Asn Glu Asp Pro Thr Ser Ser Ala Trp Asp Trp Thr Ala Asp Ala
            100                 105                 110

Thr Gln Arg Ala Met Leu Val Lys Ala Thr Gln Arg Gly Ala Val Thr
        115                 120                 125

Glu Leu Phe Ala Asn Ser Pro Met Trp Trp Met Cys Tyr Asn His Asn
    130                 135                 140

Pro Ser Gly Ala Ala Asp Gly Gly Asn Asn Leu Gln Thr Trp Asn Tyr
145                 150                 155                 160

Arg Gln His Ala Ser His Leu Ala Ala Val Ala Leu Tyr Ala Arg Thr
                165                 170                 175

Asn Trp Gly Val Asn Phe Ala Thr Val Asp Pro Phe Asn Glu Pro Ala
            180                 185                 190

Ser Ser Trp Trp Thr Ala Ser Gly Thr Gln Glu Gly Cys His Leu Asp
        195                 200                 205

Pro Ala Val Gln Ala Ala Val Leu Pro Tyr Met Arg Ser Glu Leu Asp
    210                 215                 220

Lys Arg Gly Leu Thr Gly Val Arg Ile Ser Ala Ser Asp Glu Thr Asn
225                 230                 235                 240

Tyr Asp Thr Ala Arg Ser Thr Trp Ser Ser Phe Gly Ser Ala Thr Lys
                245                 250                 255

Ala Leu Val Ser Gln Val Asn Val His Gly Tyr Gln Gly Thr Gly Gly
            260                 265                 270
```

```
Arg Arg Asp Leu Leu Tyr Thr Asp Val Val Thr Thr Ser Gly Lys Lys
        275                 280                 285

Leu Trp Asn Ser Glu Thr Gly Asp Ser Asp Gly Thr Gly Leu Ser Met
    290                 295                 300

Ala Arg Asn Leu Cys Tyr Asp Phe Arg Trp Leu His Pro Thr Ala Trp
305                 310                 315                 320

Cys Tyr Trp Gln Val Met Asp Pro Ser Thr Gly Trp Ala Met Ile Ala
                325                 330                 335

Tyr Asp Ala Asn Thr Leu Gln Pro Thr Thr Val Gln Pro Lys Tyr Tyr
            340                 345                 350

Val Met Ala Gln Phe Ser Arg His Ile Arg Pro Gly Met Thr Ile Leu
        355                 360                 365

Asp Thr Gly Val Ser Phe Ala Ala Ala Ala Tyr Asp Ala Ser Ala Arg
    370                 375                 380

Arg Leu Val Leu Val Ala Val Asn Thr Ser Thr Ser Pro Gln Thr Phe
385                 390                 395                 400

Thr Phe Asp Leu Ser Arg Phe Thr Thr Val Thr Gly Gly Ser Gly Gly
                405                 410                 415

Leu Val Pro Arg Trp Asn Thr Val Thr Gly Gly Gly Asp Met Tyr Arg
            420                 425                 430

Ala Tyr Thr Asn Thr Tyr Val Thr Gly Lys Ser Val Ser Ala Thr Phe
        435                 440                 445

Ala Ala Gly Ser Val Gln Thr Leu Gln Val Asp Gly Val Thr Thr
    450                 455                 460


<210> SEQ ID NO 8
<211> LENGTH: 458
<212> TYPE: PRT
<213> ORGANISM: Trichoderma harzianum

<400> SEQUENCE: 8

Asp Thr Thr Leu Ser Ile Asp Pro Thr Ser Asn Trp Gly Thr Trp Glu
1               5                   10                  15

Gly Trp Gly Val Ser Leu Ala Trp Trp Ala Lys Ala Phe Gly Asn Arg
            20                  25                  30

Asp Asp Leu Ala Asn Val Phe Phe Thr Arg Asn Asn Gln Val Ile Asn
        35                  40                  45

Gly Gln Asn Leu Pro Gly Leu Gly Phe Asn Ile Ala Arg Tyr Asn Ala
    50                  55                  60

Gly Ala Cys Ser Thr Asn Thr Tyr Asn Gly Ser Ser Met Val Val Ser
65                  70                  75                  80

Ser Ser Ile Lys Pro Ser Arg Gln Val Asp Gly Tyr Trp Leu Asp Trp
                85                  90                  95

Ala Ser Thr Asp Pro Ala Ser Ser Ser Trp Asn Trp Asn Val Asp Ala
            100                 105                 110

Asn Gln Arg Ala Met Leu Gln Lys Ala Lys Ala Asn Gly Ala Asn Ile
        115                 120                 125

Phe Glu Leu Phe Ser Asn Ser Pro Met Trp Trp Met Cys Leu Asn His
    130                 135                 140

Asn Pro Ser Gly Ser Gly Ser Ser Asp Asn Leu Gln Ser Trp Asn Tyr
145                 150                 155                 160

Gln Asn His Ala Val Tyr Leu Ala Asn Ile Ala Gln His Ala Gln Gln
                165                 170                 175

Asn Trp Gly Ile Gln Phe Gln Ser Val Glu Ala Phe Asn Glu Pro Ser
            180                 185                 190
```

```
Ser Gly Trp Gly Pro Thr Gly Thr Gln Glu Gly Cys His Phe Ala Val
        195                 200                 205

Ser Thr Met Ala Thr Val Ile Gly Tyr Leu Asn Thr Glu Leu Ala Gln
    210                 215                 220

Arg Gly Leu Ser Ser Phe Ile Ser Ala Ser Asp Glu Thr Ser Tyr Asp
225                 230                 235                 240

Leu Ala Ile Ser Thr Trp Gln Gly Leu Gly Ser Ser Ala Gln Asn Ala
                245                 250                 255

Val Lys Arg Val Asn Val His Gly Tyr Gln Gly Gly Gly Gly Arg Arg
            260                 265                 270

Asp Thr Leu Tyr Ser Leu Val Ser Gln Ala Gly Lys Arg Leu Trp Asn
        275                 280                 285

Ser Glu Tyr Gly Asp Ala Asp Ala Ser Gly Lys Ser Met Tyr Thr Asn
    290                 295                 300

Leu Leu Leu Asp Phe Thr Trp Leu His Pro Thr Ala Trp Val Tyr Trp
305                 310                 315                 320

Gln Ala Ile Asp Gly Ser Gly Trp Gly Leu Ile Val Gly Asp Asn Asp
                325                 330                 335

Gln Leu Thr Leu Ser Ser Ala Ser Thr Lys Tyr Phe Val Leu Ala Gln
            340                 345                 350

Leu Thr Arg His Ile Arg Pro Gly Met Gln Ile Leu Thr Thr Pro Asp
        355                 360                 365

Gly Asn Thr Val Ala Ala Tyr Asp Ser Gly Ser Gln Lys Leu Val Ile
    370                 375                 380

Val Ala Ala Asn Trp Gly Ser Ala Gln Thr Ile Thr Phe Asp Leu Thr
385                 390                 395                 400

Arg Ala Lys Thr Ala Gly Ser Asn Gly Ala Thr Val Pro Arg Trp Ser
                405                 410                 415

Thr Gln Thr Ser Gly Gly Asp Gln Tyr Lys Ser Tyr Ser Asp Thr Lys
            420                 425                 430

Ile Asn Asn Gly Lys Phe Ser Val Ser Phe Ser Thr Gly Gln Val Gln
        435                 440                 445

Thr Phe Glu Ile Ser Gly Val Val Leu Lys
    450                 455


<210> SEQ ID NO 9
<211> LENGTH: 541
<212> TYPE: PRT
<213> ORGANISM: Ascobolus stictoideus

<400> SEQUENCE: 9

Gln Thr Tyr Thr Leu Glu Ala Glu Ala Gly Thr Leu Thr Gly Val Thr
1               5                   10                  15

Val Met Asn Glu Ile Ala Gly Phe Ser Gly Thr Gly Tyr Val Gly Gly
            20                  25                  30

Trp Asp Glu Asp Ala Asp Thr Val Ser Leu Thr Phe Thr Ser Asp Ala
        35                  40                  45

Thr Lys Leu Tyr Asp Val Lys Ile Arg Tyr Ser Gly Pro Tyr Gly Ser
    50                  55                  60

Lys Tyr Thr Arg Ile Ser Tyr Asn Gly Ala Thr Gly Gly Asp Ile Ser
65                  70                  75                  80

Leu Pro Glu Thr Thr Glu Trp Ala Thr Val Asn Ala Gly Gln Ala Leu
                85                  90                  95

Leu Asn Ala Gly Ser Asn Thr Ile Lys Leu His Asn Asn Trp Gly Trp
```

-continued

```
            100                 105                 110

Tyr Leu Ile Asp Ala Val Ile Leu Thr Pro Ser Val Pro Arg Pro Pro
        115                 120                 125

His Gln Val Thr Asp Ala Leu Val Asn Thr Asn Ser Asn Ala Val Thr
    130                 135                 140

Lys Gln Leu Met Lys Phe Leu Val Ser Lys Tyr His Lys Ala Tyr Ile
145                 150                 155                 160

Thr Gly Gln Gln Glu Leu His Ala His Gln Trp Val Glu Lys Asn Val
                165                 170                 175

Gly Lys Ser Pro Ala Ile Leu Gly Leu Asp Phe Met Asp Tyr Ser Pro
            180                 185                 190

Ser Arg Val Glu Phe Gly Thr Thr Ser Gln Ala Val Glu Gln Ala Ile
        195                 200                 205

Asp Phe Asp Lys Arg Gly Gly Ile Val Thr Phe Ala Trp His Trp Asn
    210                 215                 220

Ala Pro Ser Gly Leu Ile Asn Thr Pro Gly Ser Glu Trp Trp Arg Gly
225                 230                 235                 240

Phe Tyr Thr Glu His Thr Thr Phe Asp Val Ala Ala Ala Leu Gln Asn
                245                 250                 255

Thr Thr Asn Ala Asn Tyr Asn Leu Leu Ile Arg Asp Ile Asp Ala Ile
            260                 265                 270

Ala Val Gln Leu Lys Arg Leu Gln Thr Ala Gly Val Pro Val Leu Trp
        275                 280                 285

Arg Pro Leu His Glu Ala Glu Gly Gly Trp Phe Trp Trp Gly Ala Lys
    290                 295                 300

Gly Pro Glu Pro Ala Lys Lys Leu Tyr Lys Ile Leu Tyr Asp Arg Leu
305                 310                 315                 320

Thr Asn Tyr His Lys Leu Asn Asn Leu Ile Trp Val Trp Asn Ser Val
                325                 330                 335

Ala Lys Asp Trp Tyr Pro Gly Asp Glu Ile Val Asp Val Leu Ser Phe
            340                 345                 350

Asp Ser Tyr Pro Ala Gln Pro Gly Asp His Gly Pro Val Ser Ala Gln
        355                 360                 365

Tyr Asn Ala Leu Val Glu Leu Gly Lys Asp Lys Lys Leu Ile Ala Ala
    370                 375                 380

Thr Glu Val Gly Thr Ile Pro Asp Pro Asp Leu Met Gln Leu Tyr Glu
385                 390                 395                 400

Ser Tyr Trp Ser Phe Phe Val Thr Trp Glu Gly Glu Phe Ile Glu Asn
                405                 410                 415

Gly Val His Asn Ser Leu Glu Phe Leu Lys Lys Leu Tyr Asn Asn Ser
            420                 425                 430

Phe Val Leu Asn Leu Asp Thr Ile Gln Gly Trp Lys Asn Gly Ala Gly
        435                 440                 445

Ser Ser Thr Thr Thr Val Lys Ser Thr Thr Thr Thr Pro Thr Thr Thr
    450                 455                 460

Ile Lys Ser Thr Thr Thr Thr Pro Val Thr Thr Pro Thr Thr Val Lys
465                 470                 475                 480

Thr Thr Thr Thr Pro Thr Thr Thr Ala Thr Thr Val Lys Ser Thr Thr
                485                 490                 495

Thr Thr Ala Gly Pro Thr Pro Thr Ala Val Ala Gly Arg Trp Gln Gln
            500                 505                 510

Cys Gly Gly Ile Gly Phe Thr Gly Pro Thr Thr Cys Glu Ala Gly Thr
        515                 520                 525
```

```
Thr Cys Asn Val Leu Asn Pro Tyr Tyr Ser Gln Cys Leu
    530                 535                 540


<210> SEQ ID NO 10
<211> LENGTH: 526
<212> TYPE: PRT
<213> ORGANISM: Chaetomium virescens

<400> SEQUENCE: 10

Pro Arg Asp Pro Gly Ala Thr Ala Arg Thr Phe Glu Ala Glu Asp Ala
1               5                   10                  15

Thr Leu Ala Gly Thr Asn Val Asp Thr Ala Leu Ser Gly Phe Thr Gly
            20                  25                  30

Thr Gly Tyr Val Thr Gly Phe Asp Gln Ala Ala Asp Lys Val Thr Phe
        35                  40                  45

Thr Val Asp Ser Ala Ser Thr Glu Leu Tyr Asp Leu Ser Ile Arg Val
    50                  55                  60

Ala Ala Ile Tyr Gly Asp Lys Arg Thr Ser Val Val Leu Asn Gly Gly
65                  70                  75                  80

Ala Ser Ser Glu Val Tyr Phe Pro Ala Gly Glu Thr Trp Thr Asn Val
                85                  90                  95

Ala Ala Gly Gln Leu Leu Leu Asn Gln Gly Ser Asn Thr Ile Asp Ile
            100                 105                 110

Val Ser Asn Trp Gly Trp Tyr Leu Ile Asp Ser Ile Thr Leu Thr Pro
        115                 120                 125

Ser Thr Pro Arg Pro Ala His Gln Ile Asn Glu Ala Pro Val Asn Ala
    130                 135                 140

Ala Ala Asp Lys Asn Ala Lys Ala Leu Tyr Ser Tyr Leu Arg Ser Ile
145                 150                 155                 160

Tyr Gly Lys Lys Ile Leu Ser Gly Gln Gln Glu Leu Ser Leu Ser Asn
                165                 170                 175

Trp Ile Ala Gln Gln Thr Gly Lys Thr Pro Ala Leu Val Ser Val Asp
            180                 185                 190

Leu Met Asp Tyr Ser Pro Ser Arg Val Glu Arg Gly Thr Val Gly Thr
        195                 200                 205

Ala Val Glu Glu Ala Ile Gln His His Asn Arg Gly Gly Ile Val Ser
    210                 215                 220

Val Leu Trp His Trp Asn Ala Pro Thr Gly Leu Tyr Asp Thr Glu Glu
225                 230                 235                 240

His Arg Trp Trp Ser Gly Phe Tyr Thr Ser Ala Thr Asp Phe Asp Val
                245                 250                 255

Ala Ala Ala Leu Ser Ser Thr Thr Asn Ala Asn Tyr Thr Leu Leu Ile
            260                 265                 270

Arg Asp Ile Asp Ala Ile Ala Val Gln Leu Lys Arg Leu Gln Ser Ala
        275                 280                 285

Gly Val Pro Val Leu Phe Arg Pro Leu His Glu Ala Glu Gly Gly Trp
    290                 295                 300

Phe Trp Trp Gly Ala Lys Gly Pro Glu Pro Ala Lys Lys Leu Trp Gly
305                 310                 315                 320

Ile Leu Tyr Asp Arg Val Thr Asn His His Gln Ile Asn Asn Leu Leu
                325                 330                 335

Trp Val Trp Asn Ser Ile Leu Pro Glu Trp Tyr Pro Gly Asp Ala Thr
            340                 345                 350

Val Asp Ile Leu Ser Ala Asp Val Tyr Ala Gln Gly Asn Gly Pro Met
```

-continued

```
        355                 360                 365

Ser Thr Gln Tyr Asn Gln Leu Ile Glu Leu Gly Lys Asp Lys Lys Met
    370                 375                 380

Ile Ala Ala Ala Glu Val Gly Ala Ala Pro Leu Pro Asp Leu Leu Gln
385                 390                 395                 400

Ala Tyr Glu Ala His Trp Leu Trp Phe Thr Val Trp Gly Asp Ser Phe
                405                 410                 415

Ile Asn Asn Ala Asp Trp Asn Ser Leu Asp Thr Leu Lys Lys Val Tyr
            420                 425                 430

Thr Ser Asp Tyr Val Leu Thr Leu Asp Glu Ile Gln Gly Trp Gln Gly
        435                 440                 445

Ser Thr Pro Ser Ala Thr Thr Thr Ser Ser Thr Thr Thr Pro Ser Ala
    450                 455                 460

Thr Thr Thr Thr Thr Thr Pro Ser Thr Thr Ala Thr Thr Ala Thr Pro
465                 470                 475                 480

Ser Ala Thr Thr Thr Ala Ser Pro Val Thr Tyr Ala Glu His Trp Gly
                485                 490                 495

Gln Cys Ala Gly Lys Gly Trp Thr Gly Pro Thr Thr Cys Arg Pro Pro
            500                 505                 510

Tyr Thr Cys Lys Tyr Gln Asn Asp Trp Tyr Ser Gln Cys Leu
        515                 520                 525


<210> SEQ ID NO 11
<211> LENGTH: 311
<212> TYPE: PRT
<213> ORGANISM: Bacillus sp. TY145

<400> SEQUENCE: 11

Ala Val Pro Ser Thr Gln Thr Pro Trp Gly Ile Lys Ser Ile Tyr Asn
1               5                   10                  15

Asp Gln Ser Ile Thr Lys Thr Thr Gly Gly Ser Gly Ile Lys Val Ala
            20                  25                  30

Val Leu Asp Thr Gly Val Tyr Thr Ser His Leu Asp Leu Ala Gly Ser
        35                  40                  45

Ala Glu Gln Cys Lys Asp Phe Thr Gln Ser Asn Pro Leu Val Asp Gly
    50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
        115                 120                 125

Ser Arg Thr Gly Ser Lys Val Val Ile Asn Met Ser Leu Gly Ser Ser
    130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
        195                 200                 205
```

```
Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270

His Ser Gln Leu Arg Thr Glu Leu Gln Asn Arg Ala Lys Val Tyr Asp
        275                 280                 285

Ile Lys Gly Gly Ile Gly Ala Gly Thr Gly Asp Asp Tyr Ala Ser Gly
    290                 295                 300

Phe Gly Tyr Pro Arg Val Lys
305                 310


<210> SEQ ID NO 12
<211> LENGTH: 269
<212> TYPE: PRT
<213> ORGANISM: Bacillus clausii

<400> SEQUENCE: 12

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Asp Gly Arg Gly Ala Ile Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Ser Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 13
<211> LENGTH: 480
<212> TYPE: PRT
<213> ORGANISM: Paenibacillus curdlanolyticus

<400> SEQUENCE: 13

```
Ala Asp Asn Gly Thr Ile Met Gln Tyr Phe Glu Trp Tyr Leu Pro Asn
1               5                   10                  15

Asp Gly Ala His Trp Asn Arg Leu Asn Asn Asp Ala Gln Asn Leu Lys
            20                  25                  30

Asn Val Gly Ile Thr Ala Val Trp Ile Pro Pro Ala Tyr Lys Gly Gly
        35                  40                  45

Ser Ser Ala Asp Val Gly Tyr Gly Val Tyr Asp Thr Tyr Asp Leu Gly
    50                  55                  60

Glu Phe Asn Gln Lys Gly Thr Val Arg Thr Lys Tyr Gly Thr Lys Ser
65                  70                  75                  80

Glu Leu Ile Ser Ala Val Asn Asn Leu His Ala Lys Gly Ile Ala Val
                85                  90                  95

Tyr Gly Asp Val Val Leu Asn His Arg Met Asn Ala Asp Ala Thr Glu
            100                 105                 110

Leu Val Asp Ala Val Glu Val Asp Pro Asn Asn Arg Asn Val Glu Thr
        115                 120                 125

Thr Ser Thr Tyr Gln Ile Gln Ala Trp Thr Gln Tyr Asp Phe Pro Gly
    130                 135                 140

Arg Gly Asn Thr Tyr Ser Ser Phe Lys Trp Arg Trp Tyr His Phe Asp
145                 150                 155                 160

Gly Val Asp Trp Asp Gln Ser Arg Gly Leu Asn Arg Ile Tyr Lys Leu
                165                 170                 175

Arg Gly Asp Gly Lys Asp Trp Asp Trp Glu Val Asp Ser Glu Tyr Gly
            180                 185                 190

Asn Tyr Asp Tyr Leu Met Gly Ala Asp Leu Asp Phe Asn His Pro Asp
        195                 200                 205

Val Val Asn Glu Thr Lys Thr Trp Gly Lys Trp Phe Val Asn Thr Val
    210                 215                 220

Asn Leu Asp Gly Val Arg Leu Asp Ala Val Lys His Ile Lys Phe Asp
225                 230                 235                 240

Phe Met Arg Asp Trp Val Asn Asn Val Arg Ser Thr Thr Gly Lys Asn
                245                 250                 255

Leu Phe Ala Val Gly Glu Tyr Trp His Tyr Asp Val Asn Lys Leu Asn
            260                 265                 270

Ser Tyr Ile Thr Lys Thr Asn Gly Thr Met Ser Leu Phe Asp Val Pro
        275                 280                 285

Leu His Phe Arg Phe Tyr Asp Ala Ser Asn Gly Gly Gly Gly Tyr Asp
    290                 295                 300

Met Arg Asn Leu Leu Asn Asn Thr Leu Met Ser Ser Asn Pro Met Lys
305                 310                 315                 320

Ala Val Thr Phe Val Glu Asn His Asp Thr Gln Pro Thr Gln Ala Leu
                325                 330                 335

Gln Ser Thr Val Gln Ser Trp Phe Lys Pro Leu Ala Tyr Ala Thr Ile
            340                 345                 350

Leu Thr Arg Glu Gln Gly Tyr Pro Cys Val Phe Tyr Gly Asp Tyr Tyr
        355                 360                 365

Gly Thr Ser Asp Gly Lys Ile Ser Ser Tyr Lys Pro Ile Met Asp Lys
```

```
    370                 375                 380

Leu Leu Asn Ala Arg Lys Val Tyr Ala Tyr Gly Thr Gln Arg Asp Tyr
385                 390                 395                 400

Phe Asp His Pro Asp Ile Val Gly Trp Thr Arg Glu Gly Asp Ala Ala
                405                 410                 415

His Ala Gly Ser Gly Leu Ala Thr Leu Ile Thr Asp Gly Pro Gly Gly
            420                 425                 430

Ser Lys Trp Met Tyr Val Gly Thr Ser Lys Ala Gly Gln Val Trp Thr
        435                 440                 445

Asp Lys Thr Gly Asn Arg Ser Gly Thr Val Thr Ile Asp Ala Asn Gly
    450                 455                 460

Trp Gly Asn Phe Trp Val Asn Gly Gly Ser Val Ser Val Trp Ala Lys
465                 470                 475                 480


<210> SEQ ID NO 14
<211> LENGTH: 269
<212> TYPE: PRT
<213> ORGANISM: Thermomyces lanuginosus

<400> SEQUENCE: 14

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```